(12) United States Patent
Gupta et al.

(10) Patent No.: US 11,804,307 B2
(45) Date of Patent: Oct. 31, 2023

(54) SYSTEMS AND METHODS FOR DYNAMIC SURVEILLANCE OF MEDICATION AND ANTIMICROBIAL RESISTANCE TRENDS

(71) Applicant: Becton, Dickinson and Company, Franklin Lakes, NJ (US)

(72) Inventors: Vikas Gupta, Naperville, IL (US); John Murray, Atlanta, GA (US); Kalvin Yu, Venice, CA (US); Hanna Jokinen-Gordon, Smyrna, GA (US); Willem Folkerts, Westminster, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 162 days.

(21) Appl. No.: 17/182,835

(22) Filed: Feb. 23, 2021

(65) Prior Publication Data
US 2021/0287809 A1    Sep. 16, 2021

Related U.S. Application Data

(60) Provisional application No. 62/981,439, filed on Feb. 25, 2020.

(51) Int. Cl.
| G16H 50/50 | (2018.01) |
| G16H 70/20 | (2018.01) |
| G16H 50/70 | (2018.01) |

(52) U.S. Cl.
CPC .......... *G16H 50/50* (2018.01); *G16H 50/70* (2018.01); *G16H 70/20* (2018.01)

(58) Field of Classification Search
CPC ........ G16H 50/50; G16H 50/70; G16H 70/20; Y02A 90/10
See application file for complete search history.

(56) References Cited

U.S. PATENT DOCUMENTS 8,512,723 B2 *  8/2013  Scholz .................. A61K 47/20
                                                        514/557
9,069,887 B2   6/2015  Gupta et al.
(Continued)

OTHER PUBLICATIONS

E. Liu, Xiang. Operations Research Models for Reducing Hospital Readmissions. University of Michigan, 2019 (Year: 2019).*
(Continued)

*Primary Examiner* — Amber A Misiaszek
(74) *Attorney, Agent, or Firm* — Knobbe Martens Olson & Bear LLP

(57) ABSTRACT

Systems and methods for selecting a treatment regimen for a particular patient are provided. The treatment regimen is selected using a first data store including a first plurality of patient records for a first plurality of patients, and a second data store including efficacy rates of a plurality of treatment regimens against a plurality of infections and infection-causing pathogens. The system, or a user of the system, identifies a first infection of the particular patient and a first treatment regimen to be prescribed to treat the first infection. A second plurality of patient records is generated by identifying, in the first plurality of patient records of the first data store, patient records associated with diagnosis or treatment of the first infection. The second plurality of patient records are appended with efficacy rates for the first infection from the second data store. Systems and methods of the present disclosure can use these appended records to generate a dynamic model configured to determine a likelihood estimation that the first treatment regimen is an appropriate treatment regimen to treat the first infection.

12 Claims, 12 Drawing Sheets

(56) References Cited

U.S. PATENT DOCUMENTS

| | | | | |
|---|---|---|---|---|
| 2004/0010418 | A1* | 1/2004 | Buonocore | G16H 40/63 |
| | | | | 705/2 |
| 2008/0177578 | A1 | 7/2008 | Zakim | |
| 2010/0274495 | A1* | 10/2010 | Sobol | G16H 10/20 |
| | | | | 702/19 |
| 2011/0093249 | A1* | 4/2011 | Holmes | G16H 50/50 |
| | | | | 703/6 |
| 2012/0116794 | A1* | 5/2012 | Wilkerson-Amendell | |
| | | | | G16H 10/65 |
| | | | | 705/2 |
| 2014/0052475 | A1* | 2/2014 | Madan | G16H 50/30 |
| | | | | 705/3 |
| 2019/0172584 | A1 | 6/2019 | Athey et al. | |
| 2020/0035359 | A1 | 1/2020 | Erpenbach et al. | |
| 2021/0012326 | A1* | 1/2021 | Maxwell Zelocchi | H04L 9/50 |
| 2021/0012894 | A1* | 1/2021 | Zelocchi | G16H 10/60 |

OTHER PUBLICATIONS

Dunne et al., "A patient-specific clinical predictive model to anticipate the risk of treatment failure in uncomplicated urinary tract infections", Poster # P1656, 29th European Congress of Clinical Microbiology and Infectious Diseases; Apr. 13-16, 2019; Amsterdam, NL; 1 page.

Lodise et al., "Prevalence and Regional Variation in ESBLs and CRE Enterobacteriaceae (ENT) Among Hospitalized Adult Patients with ENT on a Urine Culture: A Multicenter Evaluation", Poster #1440; ID Week, Oct. 4, 2019; Washington, D.C.; 1 page.

Puzniak et al., "A Combination Antibiogram Evaluation for *Pseudomonas aeruginosa* in Respiratory and Blood Sources from Intensive Care Unit (ICU) and Non-ICU Settings in U.S. Hospitals", Antimicrobial Agents Chemotherapy; Apr. 2019; vol. 63, Issue 4, e02564-18; 16 pages.

Tabak et al., "Predicting Readmission of Early Hospitalization Using Electronic Clinical Data—An Early Readmission Risk Score", Medical Care; Mar. 2017; vol. 55, No. 3; pp. 267-275.

Tabak et al., "Hospital-level high-risk antibiotic use in relation to hospital-associated *Clostridioides difficile* infections: Retrospective analysis of 2016-2017 data from US hospitals", Infection Control & Hospital Epidemiology; Sep. 2019; 40: pp. 1229-1235.

International Search Report and Written Opinion dated May 7, 2021 for International Application No. PCT/US2021/019250 dated Feb. 23, 2021.

Dunne et al., "Impact of ESBL-positivity and Quinolone Non-susceptibility on Outcome for Inpatients with Complicated Urinary Tract Infection: A Multicenter Evaluation in the US", Poster; Iterum Therapeutics, (2018) 1 page.

Gupta et al., "A Multicenter Evaluation of the US Prevalence and Regional Variation in Macrolide—Resistant *S. pneumoniae* in Ambulatory and Hospitalized Adult Patients in the United States", In Open Forum Infectious Diseases (vol. 8, No. 7, p. ofab063). US: Oxford University Press (Jul. 2021); 5 pages.

Kaye et al., "Antimicrobial Resistance Trends in Urine *Escherichia coli* Isolates from Adult and Adolescent Females in the United States from 2011 to 2019: Rising ESBL Strains and Impact on Patient Management", Clin Infect Dis. Dec. 1, 2021; 73(11): 1992-1999.

McCann et al., "Carbapenem-nonsusceptible Gram-negative Pathogens in ICU and Non-ICU Settings in US Hospitals in 2017: A Multicenter Study", In *Open forum infectious diseases* (vol. 5, No. 10, p. ofy241). US: Oxford University Press (2018); 15 pages.

Pogue et al., "Susceptibility of Ceftolozane/Tazobactam (C/T) to Multi Drug Resistant (MDR) *Pseudomonas aeruginosa* (PSA) Clinical Isolates in Hospitalized Patients: A Multicenter Evaluation", Poster; ASM Microbe 2017, Jun. 1-5, 2017, © 2008 Merck Sharp & Dohme Corp., 1 page.

Puzniak et al., "Initial Treatment Selection among Patients with Recurrent *Pseudomonas aeruginosa* (PSA) Infections: Does Prior PSA Antibiotic Susceptibility Affect Subsequent Empiric Treatment Decisions?", Poster #2270, In *Open Forum Infectious Diseases* (vol. 6), Oct. 5, 2019, © 2019 Merck Sharp & Dohme Corp., 1 page.

Puzniak et al., "Effect of Inadequate Empiric Antibacterial Therapy on Hospital Outcomes in SARS-COV-2-positive and -negative US Patients with a Positive Bacterial Culture: A Multicenter Evaluation from Mar. to Nov. 2020", In *Open forum infectious diseases*, (vol. 8, No. 6, p. ofab232). US: Oxford University Press Jun. 2021, 9 pages.

Tabak et al., "Predicting the Risk for Hospital-Onset *Clostridium difficile* Infection (HO-CDI) at the Time of Inpatient Admission: HO-CDI Risk Score", Infection Control & Hospital Epidemiology. Jun. 2015, 36(6): 695-701.

Tillotson et al., "Pathogen Type and Inappropriate Empiric Therapy (IET) in Culture-positive Skin and Soft Tissue Infection among Hospitalized Patients in the US, 2015-2017", Poster #569, ASM Microbe 2018, Atlanta, GA—USA, Jun. 7-11, 2018, 1 page.

\* cited by examiner

| Region | Carb-NS Enterobacteriaceae | | Carb-NS P. aeruginosa | | Carb-NS Acinetobacter spp | |
|---|---|---|---|---|---|---|
| | Number tested | % NS | Number tested | % NS | Number tested | % NS |
| Region 1 | 29,821 | 2.2% | 5,359 | 13.4% | 404 | 53.5% |
| Region 2 | 43,791 | 0.9% | 6,123 | 17.1% | 462 | 37.7% |
| Region 3 | 8,422 | 0.4% | 1,164 | 3.8% | 43 | 2.3% |
| Region 4 | 10,485 | 0.2% | 1,423 | 8.6% | 63 | 9.5% |

NS = non-susceptible

Figure 1B

Distribution of Carb-NS Isolates by Region

Geographic incidence rate (per 1000 admissions) of non-duplicate Pathogen X urine isolates in hospitalized patients

|  | Appropriate (number) | Inappropriate (number) | Initial Inappropriate Therapy (%) |
|---|---|---|---|
| Total | 14,359 | 2,000 | 12.2 |
| Class A | 10,203 | 869 | |
| Antibiotic A1 | 5,598 | 454 | 7.5 |
| Antibiotic A2 | 2,867 | 240 | 7.7 |
| Antibiotic A3 | 1,082 | 79 | 6.8 |
| Antibiotic A4 | 347 | 29 | 7.7 |
| Antibiotic A5 | 309 | 67 | 17.8 |
| Class B | 2,400 | 701 | |
| Antibiotic B1 | 1,331 | 386 | 22.4 |
| Antibiotic B2 | 547 | 162 | 22.8 |
| Antibiotic B3 | 309 | 78 | 24.0 |
| Antibiotic B4 | 213 | 75 | 20.1 |
| Class C | 1,567 | 8 | |
| Antibiotic C1 | 1,225 | 8 | 0.5 |
| Antibiotic C2 | 342 | 0 | 0.0 |
| Antibiotic D | 2 | 345 | 99.4 |
| Antibiotic E | 187 | 77 | 29.1 |

Figure 1E

Initial Empiric Antibiotic Therapy for cUTI Caused by Pathogen Y

| Characteristic | Inappropriate Therapy N=2,000 | Appropriate Therapy N=14,359 |
|---|---|---|
| Bacteremia (%) | 7.6 | 12.9 |
| ICU (%) | 20.1 | 23.4 |

Figure 1F

Clinical Features of Patients with cUTI Caused by Pathogen Y

| Antibiotic | Gram Negative (GN) Infections Only | | Gram Positive (GP) Infections Only | | Mixed GN/GP Infections | | Overall | |
|---|---|---|---|---|---|---|---|---|
| | IET | Total | IET | Total | IET | Total | IET | Total |
| Total Admissions | 270 (22.8%) | 1,184 | 381 (6.5%) | 5,891 | 633 (22.8%) | 2,778 | 1,284 (13.0%) | 9,853 |
| Antibiotic A | 126 (46.7%) | 126 (10.6%) | 27 (7.0%) | 4,166 (70.7%) | 117 (18.5%) | 1,333 (48.0%) | 270 (21.0%) | 5,624 (57.1%) |
| Antibiotic B | 42 (15.6%) | 566 (47.8%) | 112 (29.4%) | 1,600 (27.2%) | 47 (7.4%) | 1,332 (47.9%) | 201 (15.7%) | 3,498 (35.5%) |
| Antibiotic C | 30 (11.1%) | 30 (2.5%) | 41 (10.8%) | 558 (9.5%) | 41 (6.5%) | 139 (5.0%) | 112 (8.7%) | 727 (7.4%) |
| Antibiotic D | 6 (2.2%) | 134 (11.3%) | 36 (9.4%) | 264 (4.5%) | 22 (3.5%) | 264 (9.5%) | 64 (5.0%) | 662 (6.7%) |
| Antibiotic E | 18 (6.7%) | 107 (9.0%) | 31 (8.1%) | 346 (5.9%) | 27 (4.3%) | 188 (6.8%) | 76 (5.9%) | 641 (6.5%) |
| Antibiotic F | 9 (3.3%) | 133 (11.2%) | 25 (6.6%) | 189 (3.2%) | 8 (1.3%) | 277 (10.0%) | 42 (3.3%) | 599 (6.1%) |
| Antibiotic G | 18 (6.7%) | 66 (5.6%) | 12 (3.1%) | 286 (4.9%) | 11 (1.7%) | 190 (6.8%) | 41 (3.2%) | 542 (5.5%) |
| Antibiotic H | 17 (6.3%) | 35 (3.0%) | 39 (10.2%) | 347 (5.9%) | 19 (3.0%) | 109 (3.9%) | 75 (5.8%) | 491 (5.0%) |
| Antibiotic I | 16 (5.9%) | 24 (2.0%) | 14 (3.7%) | 269 (4.6%) | 12 (1.9%) | 123 (4.4%) | 42 (3.3%) | 416 (4.2%) |
| Antibiotic J | 7 (2.6%) | 7 (0.6%) | 1 (0.3%) | 198 (3.4%) | 4 (0.6%) | 78 (2.8%) | 12 (0.9%) | 283 (2.9%) |
| Antibiotic K | 6 (2.2%) | 6 (0.5%) | | 137 (2.3%) | 5 (0.8%) | 75 (2.7%) | 11 (0.9%) | 218 (2.2%) |
| Antibiotic L | 7 (2.6%) | 35 (3.0%) | 3 (0.8%) | 90 (1.5%) | 5 (0.8%) | 80 (2.9%) | 15 (1.2%) | 205 (2.1%) |
| Antibiotic M | 6 (2.2%) | 8 (0.7%) | 2 (0.5%) | 118 (2.0%) | 3 (0.5%) | 26 (0.9%) | 11 (0.9%) | 152 (1.5%) |
| Antibiotic N | 1 (0.4%) | 15 (1.3%) | 2 (0.5%) | 91 (1.5%) | 7 (1.1%) | 45 (1.6%) | 10 (0.8%) | 151 (1.5%) |
| Antibiotic O | 1 (0.4%) | 28 (2.4%) | 10 (2.6%) | 51 (0.9%) | 5 (0.8%) | 59 (2.1%) | 16 (1.2%) | 138 (1.4%) |
| Antibiotic P | 4 (1.5%) | 10 (0.8%) | 1 (0.3%) | 79 (1.3%) | 4 (0.6%) | 32 (1.2%) | 9 (0.7%) | 121 (1.2%) |
| Antibiotic Q | 4 (1.5%) | 21 (1.8%) | 2 (0.5%) | 40 (0.7%) | 3 (0.5%) | 52 (1.9%) | 9 (0.7%) | 113 (1.1%) |
| Antibiotic R | 20 (7.4%) | 20 (1.7%) | 31 (8.1%) | 31 (0.5%) | 52 (8.2%) | 52 (1.9%) | 103 (8.0%) | 103 (1.0%) |
| Antibiotic S | 4 (1.5%) | 16 (1.4%) | 3 (0.8%) | 52 (0.9%) | 1 (0.2%) | 35 (1.3%) | 8 (0.6%) | 103 (1.0%) |

Figure 1G

Inappropriate Empiric Therapy (IET) by Antibiotic and Pathogen Category

Figure 1H

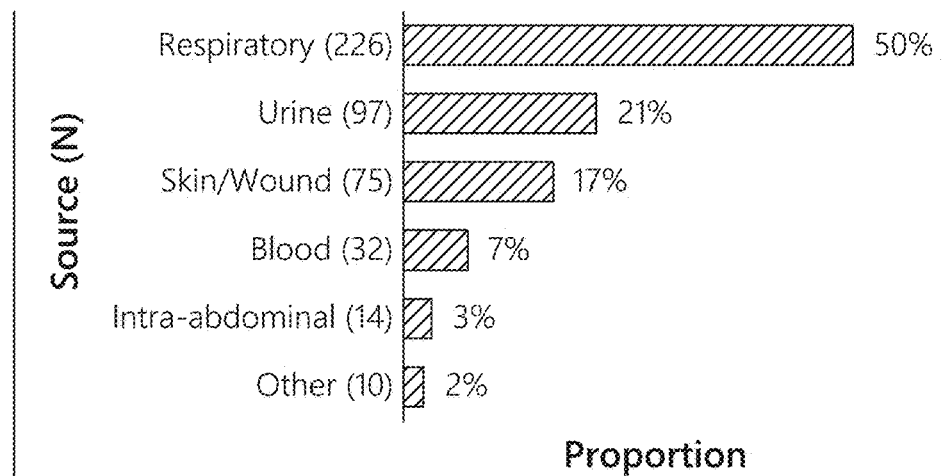

Source Distribution for non-duplicate PSA (*Pseudomonas aeruginosa*) isolates tested to C/T (Ceftolozane/Tazobactam)

Figure 1I

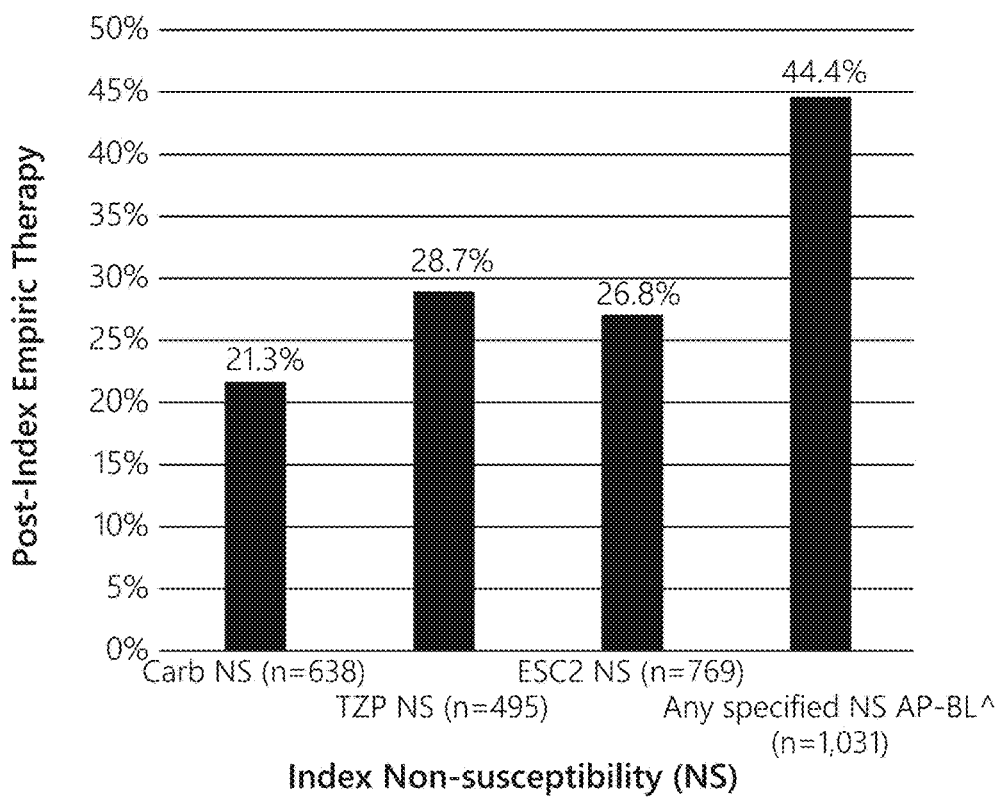

AP-BL=antipseudomonal beta-lactam; Carb=carbapenem;
ESC2= extended-spectrum cephalosporins; TZP = piperacillin/tazobactam
^Carb, TZP, or ESC2

Anti-pseudomonal beta-lactams prescribed as empiric therapy in post-index PSA admissions by index PSA infection NS status

SYSTEMS AND METHODS FOR DYNAMIC SURVEILLANCE OF MEDICATION AND ANTIMICROBIAL RESISTANCE TRENDS

CROSS-REFERENCE TO RELATED APPLICATIONS

This application claims the benefit of U.S. Provisional Application No. 62/981,439, filed Feb. 25, 2020, which is hereby incorporated by reference in its entirety.

TECHNICAL FIELD

Embodiments of the present disclosure relate to systems and methods providing dynamic situational awareness of resistance rates of specific pathogens, success rates of specific antibiotic regimens to treat drug-resistant pathogens, susceptibility rates of relevant pathogens to new antibiotic regimens on a patient-specific, facility-specific, and region-specific basis. Systems and methods of the present disclosure include data processing, including database and file management, as well as a database system for optimizing treatment protocols and improving patient outcomes based on real-time data on resistance rates, treatment success rates, and susceptibility rates and treatment outcome analytics.

BACKGROUND

The rate of growth and spread of antibiotic-resistant infections continues to increase at an alarming pace. Approximately 2.8 million antibiotic resistant infections occur each year in the United States, killing 35,000 people. While progress has been made to understand and decrease the spread of antibiotic-resistant infections (or so-called "superbugs"), the threat of untreatable infectious diseases caused by bacteria and microbes that can spread rapidly continues to grow. Drug resistance is commonly associated with misuse and overuse of antibiotics and other microbial treatments, which cause bacteria to evolve into treatment-resistant strains. Addressing antibiotic resistance is vitally important to ensure lifesaving medications are effective and delivered in a timely manner, improving patient outcomes.

SUMMARY

The systems, methods, and devices described herein each have several aspects, no single one of which is solely responsible for its desirable attributes. Without limiting the scope of this disclosure, several non-limiting features will now be described briefly.

Embodiments of the present disclosure relate to a database system (also herein referred to as "the system") for merging and analyzing data from discrete and changing data sets and dynamically generating and applying customized models based on the merged data. Electronic databases of the present disclosure provide for storage and retrieval of digital data records. Data records in such databases may be electronically and automatically updated and processed in real-time without human intervention.

In one aspect, a system for selecting a treatment regimen for a particular patient is provided. The system includes a first data store including a first plurality of patient records for a first plurality of patients; a second data store including efficacy rates of a plurality of treatment regimens against a plurality of infections and infection-causing pathogens; and a hardware processor. The hardware processor is configured to execute computer-executable instructions to: receive, from a user, an indication of a first infection of the particular patient and a first treatment regimen to be prescribed to treat the first infection; generate a first database including a second plurality of patient records by identifying, in the first plurality of patient records of the first data store, patient records associated with diagnosis or treatment of the first infection; generate a second database including the second plurality of patient records appended with efficacy rates for the first infection from the second data store; and generate a dynamic model configured to determine a likelihood estimation that the first treatment regimen is an appropriate treatment regimen to treat the first infection. The dynamic model is configured to: identify, based on the second database, a first efficacy rate of the first treatment regimen to treat the first infection; and identify, from the second database, a second efficacy rate of a second treatment regimen to treat the first infection. The hardware processor is further configured to execute computer-executable instructions to generate a first alert to the user when the identified first efficacy rate is less than a first threshold level or the identified second efficacy rate is greater than a second threshold level. The first data store can be continuously populated with additional patient records. The hardware processor can be further configured to dynamically and automatically execute computer-executable instructions to: update the first database and the second database based on patient records of the additional patient records that are associated with the first infection; and update the first efficacy rate and the second efficacy rate.

The computer-executable instructions can be further configured to receive, from a user, an indication of a healthcare facility, wherein the second plurality of patient records identified by the computer-executable instructions are patient records associated with the first infection and the indicated healthcare facility.

The computer-executable instructions can be further configured to receive, from a user, an indication of a geographic region, wherein the second plurality of patient records identified by the computer-executable instructions are patient records associated with the first infection and the indicated geographic region.

The computer-executable instructions can be further configured to receive, from a user, an indication of a time period, wherein the second plurality of patient records identified by the computer-executable instructions are patient records associated with diagnosis or treatment of the first infection within the indicated time period.

The computer-executable instructions can be configured to filter the second plurality of patient records appended with efficacy rates to include patient records associated with at least one of a particular treatment regimen of plurality of treatment regimens, infections related to the first infection, a geographic region, and a healthcare facility.

The computer-executable instructions can be further configured to generate a second alert to the user if, after updating the first efficacy rate and the second efficacy rate, the first efficacy rate falls below the first threshold or the second efficacy rate rises above the second threshold.

In another aspect, a computer-implemented method is provided. The computer-implemented method selects a treatment regimen for a particular patient using a first data store including a first plurality of patient records for a first plurality of patients and a second data store including efficacy rates of a plurality of treatment regimens against a plurality of infections and infection-causing pathogens. The computer-implemented method includes, under control of one or more processors: receiving an indication of a first infection of the particular patient and a first treatment regimen to be prescribed to treat the first infection; generating a first database including a second plurality of patient records by identifying, in the first plurality of patient records of a first data store, patient records associated with diagnosis or treatment of the first infection; generating a second database including the second plurality of patient records appended with efficacy rates for the first infection from the second data store; and generating a dynamic model configured to determine a likelihood estimation that the first treatment regimen is an appropriate treatment regimen to treat the first infection. The dynamic model is further configured to: identify, based on the second database, a first efficacy rate of the first treatment regimen to treat the first infection; and identify, from the second database, a second efficacy rate of a second treatment regimen to treat the first infection. The computer-implemented method further includes, under control of one or more processors, receiving generate a first alert when the identified first efficacy rate is less than a first threshold level or the identified second efficacy rate is greater than a second threshold level.

The first data store can be continuously populated with additional patient records, and the computer-implemented method can further include: updating the first database and the second database based on patient records of the additional patient records that are associated with the first infection; and updating the first efficacy rate and the second efficacy rate.

The computer-implemented method can further include receiving an indication of a healthcare facility, wherein the second plurality of patient records are patient records associated with the first infection and the indicated healthcare facility.

The computer-implemented method can further include receiving an indication of a geographic region, wherein the second plurality of patient records are patient records associated with the first infection and the indicated geographic region.

The computer-implemented method can further include receiving an indication of a time period, wherein the second plurality of patient records are patient records associated with diagnosis or treatment of the first infection within the indicated time period.

The computer-implemented method can further include filtering the second plurality of patient records appended with efficacy rates to comprise patient records associated with at least one of a particular treatment regimen of plurality of treatment regimens, infections related to the first infection, a geographic region, and a healthcare facility.

The computer-implemented method can further include generating a second alert if, after updating the first efficacy rate and the second efficacy rate, the first efficacy rate falls below the first threshold or the second efficacy rate rises above the second threshold.

Additional embodiments of the disclosure are described below in reference to the appended claims, which may serve as an additional summary of the disclosure.

In various embodiments, computer systems are disclosed that include one or more hardware computer processors in communication with one or more non-transitory computer readable storage devices, wherein the one or more hardware computer processors are configured to execute the plurality of computer executable instructions in order to cause the computer system to perform operations comprising one or more aspects of the above-described embodiments (including one or more aspects of the appended claims).

In various embodiments, computer-implemented methods are disclosed in which, under control of one or more hardware computing devices configured with specific computer executable instructions, one or more aspects of the above-described embodiments (including one or more aspects of the appended claims) are implemented and/or performed.

In various embodiments, computer readable storage mediums storing software instructions are disclosed, wherein, in response to execution by a computing system having one or more hardware processors, the software instructions configure the computing system to perform operations comprising one or more aspects of the above-described embodiments (including one or more aspects of the appended claims).

Although certain embodiments and examples are disclosed below, the inventive subject matter extends beyond the specifically disclosed embodiments to other alternative embodiments and/or uses and to modifications and equivalents thereof. Thus, the scope of the application is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

BRIEF DESCRIPTION OF THE DRAWINGS

The above-mentioned aspects, as well as other features, aspects, and advantages of the present technology will now be described in connection with various aspects, with reference to the accompanying drawings. The illustrated aspects, however, are merely examples and are not intended to be limiting.

The figures depicted herein and the corresponding descriptions may utilize examples involving patients, doctors, other care providers such as nurses, pharmacists, and microbiologists, medications, diseases and illnesses, and corresponding entities and records. However, these entities and records may be replaced with other entities and records.

FIGS. 1B-1I are example tables and diagrams that can be implemented in the data flow diagram of the medication database system of FIG. 1A, according to an embodiment;

DETAILED DESCRIPTION OF EMBODIMENTS

Figure 1A:
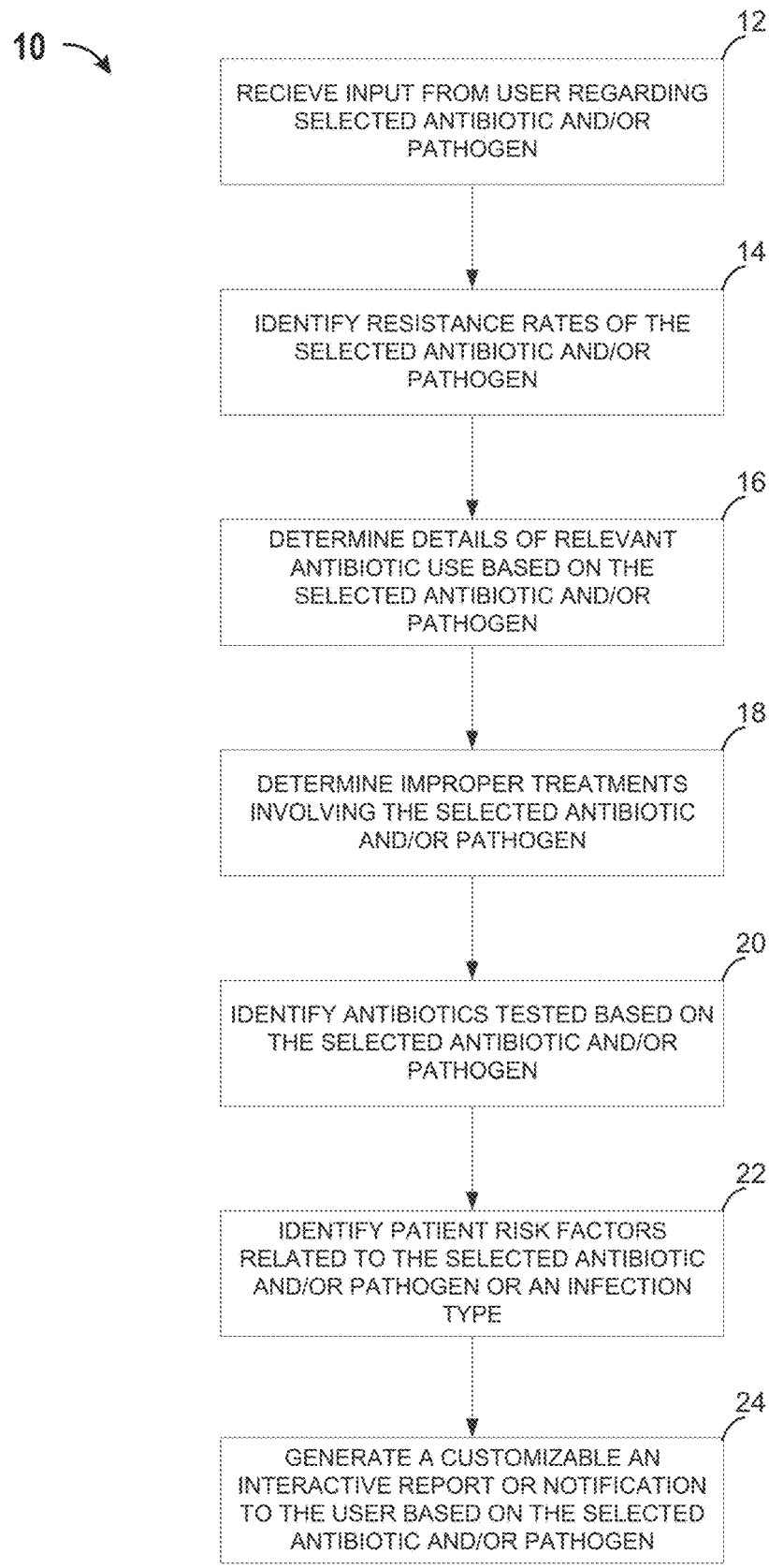
FIG. 1A is a block or data flow diagram of a medication database system for providing electronic notifications regarding database records, according to an embodiment.

System and methods of the present disclosure advantageously implement antimicrobial stewardship and antimicrobial resistance (AMR) goals at various levels, including at a patient-specific level, a facility-specific level, and a region-specific level. The systems and methods of the present disclosure provide dynamic, real-time insights and situational awareness to clinical staff on medication and antimicrobial resistance trends at three core levels: regional insights and situational awareness, facility-specific insights and situational awareness, and patient-specific insights and situational awareness.

Doctors, nurses, pharmacists, medical staff, medical administrators, medical researchers, and other entities involved in diagnosing and treating infectious diseases (hereinafter referred to as medical entities) understand the public health threat of drug resistant infections and that misuse and overuse of particular medications can increase such resistances. Medical entities can receive updated drug efficacy information, but at very infrequent intervals (for example, every 5-7 years) and based on aggregated data that spans wide timeframes and geographic areas. Additionally, when diagnosing and prescribing medication to a patient, a clinician, such as a doctor, may not realize which available treatment regimens, including type and dosage of medication, may be appropriate or inappropriate (for example, which treatment regimens have been empirically and clinically demonstrated to be effective to resolve an infection and which have not).

Further, the doctor may be evaluating treatment regimens on the basis of symptoms presented by a patient, before an infection has been diagnosed. In some cases, the doctor may not have sufficient knowledge of prior infection and treatment information for the patient. For example, the patient being diagnosed by the doctor may have traveled to the doctor's healthcare facility from a different geographic region, or may have been infected while travelling or visiting a different geographic region. As such, the doctor may have insufficient or inaccurate information about the origin and type of pathogen causing infection (and, in particular, to what treatment regimens the pathogen is resistant or susceptible). As a result, the doctor may diagnose an infection and prescribe a treatment regimen based on the geographic region of the doctor's facility, and information the doctor can contemporaneously glean from the patient. As such, the doctor may rely on diagnostic test results (for example, blood tests, cultures, bacterial identification, and susceptibility testing, etc.), which can take time and delay information that the doctor needs to accurately diagnose infectious disease and prescribe appropriate treatment regimens. Thus, the doctor may not know whether the pathogen causing the infection originated from a geographic region where the pathogen is more or less resistant to the treatment regimens than in other areas, whether a specific patient has a history of prior infections caused by the same pathogen, whether a specific patient has a history of resistance to treatment of that pathogen (for reasons related or unrelated to the pathogen), and/or whether the doctor's previous diagnosis and prescriptions for the same or similar infections have been successfully resolved or not, any of which may be instructive regarding what treatment regimen the doctor should prescribe to the patient.

To accurately diagnose infectious disease and prescribe effective treatment regimens, medical entities need to receive accurate information dynamically and in real-time. Information received after the patient is diagnosed and a treatment regimen has been prescribed is not as useful as information received during diagnosis and before a treatment regimen is prescribed. Additionally, providing information regarding how often a doctor prescribes an effective treatment regimen can be useful in allowing doctors to adapt their practices to improve patient care by identifying misuse or overuse of antibiotic medications, and allowing the doctors to identify how to adapt to improve patient care.

Doctors that are prescribing inappropriate treatment regimens may not know how to correct or improve their standards of care. The doctors may not realize that they have different choices for medications that have efficacy rates that changed since the doctors last researched or received updates on efficacy rates. Additionally, the doctors, when treating a particular current patient, the doctors may not know if treatment regimens they selected successfully resolved infectious disease in previous patients (for example, whether their previous patients have recovered from infections by administration of the prescribed type and dose of medication). For instance, while a doctor remembers that a previous patient presented with an infection X and that the doctor prescribed treatment regimen A, the doctor likely is not informed whether the prescribed treatment regimen resolved infection X of the previous patient. Thus, the doctor may prescribe the treatment regimen A to a current patient exhibiting symptoms of infection X without knowing whether the treatment regimen A is effective against the infection X, or whether there are other factors to consider (for example, that the current patient has a history of resistance to treatment using medication A, that the current patient contracted the infection X in a geographic region known to have strains of infection X that are resistant to medication A, and so forth). Furthermore, resources will be inevitably duplicated in the process of diagnosing (or rediagnosing) an infection, and where along the clinical spectrum that infection is: partially treated, near completed treatment, or failed treatment. The mitigation of resource duplication adds to the overall financial value proposition as well as aiding in expedited patient safety and care.

Embodiments of the systems and methods of the present disclosure provide medical entities with dynamically-updated information in the diagnosis stage and/or the prescription stage of patient care, thereby allowing the doctor to tailor and adapt a prescribed therapy to improve care to a particular patient's current circumstances while taking into account recent past therapy. The systems and methods of the present disclosure use real-time or near real-time data inputs from a variety of data stores and use these data inputs to focus specifically on a current patient and the current patient's specific needs and circumstances. The data inputs relate to the facility-specific and region-specific insights, in addition to patient-specific insights. As a non-limiting example, if the patient was infected with a pathogen while traveling in a foreign country, the systems and methods may analyze records of similar infections caused by that same pathogen in the foreign country to account for outcome-dependent variables (for example, drug resistance, different strains of the pathogen, etc.) in prescribing a treatment regimen.

Furthermore, in many instances, doctors may not know which tests to order to identify an infection-causing pathogen for particular patients. For example, testing whether a particular infection-causing pathogen is resistant to a particular treatment regimen may be more useful when the patient has a history of resistance to traditional therapies of that or similar pathogens. However, if a doctor is informed that a first patient may be infected with a drug-resistant strain of pathogen A, and a second patient is infected with a non-drug resistant strain of pathogen A, the doctor may treat the first patient using a different treatment regimen than that prescribed to the second patient, for example by ordering additional blood culture tests from the first patient to test for drug resistance to other antibiotics but not using valuable, limited blood culture testing resources to test for drug resistance in the second patient. Additionally, the doctor may prescribe different treatment regimens to the first patient and the second patient based on the identified or suspected drug resistances.

Overview of Dynamically-Updated Parameters

Implementations of the present disclosure address the above-described deficiencies in information flow and situational awareness in treating infection diseases. Systems and methods described herein provide dynamically-updated regional, facility, and patient specific insights and analytics in five parameters directly related to antimicrobial stewardship and diagnostic resource stewardship. Although reference is made to "a doctor" or "a particular doctor" throughout this disclosure, it will be understood that embodiments of the systems and methods described herein provide dynamic insights and situational awareness to any medical entity involved in patient care.

Parameter 1: Resistance Rates of Specific Pathogens or Infections

In a first step, systems and methods of the present disclosure inform a medical entity, using dynamically-updated data, if resistance rates to specific pathogens or infections are high in the particular entity's facility and in the particular entity's geographic region within a defined timeframe. Insights relating to this parameter can be based on data collected over a timeframe of the doctor's choosing or a timeframe established by the doctor's facility, a regulatory agency, or any other entity. In one non-limiting example, the timeframe is the quarter or a three month period ending on the date the doctor requested or received the dynamically-updated data. Other example timeframes include the prior day, the prior week, the prior two weeks, the prior month, the prior two months, the prior six months, and the prior year. It will be understood that any suitable timeframe can be implemented in embodiments of the present disclosure. The data can be provided to the doctor in various forms. In one non-limiting example where the timeframe is the prior quarter, the doctor identifies an antibiotic treatment regimen the doctor is considering to prescribe to a particular patient.

In response to the receipt of the identified antibiotic, systems and methods of the present disclosure can display to the doctor quarterly heatmaps for relevant or highly-active multi-drug resistant (MDR) pathogens that can be treated using the selected antibiotic. Example MDR pathogens include, but are not limited to, carbapenem-resistant Enterobacteriaceae (CRE) and *Acinetobacter baumannii* (ACB). Systems and methods of the present disclosure can display quarter heatmaps for urine, skin/wound, or respiratory cultures positive for a relevant or highly active MDR pathogen. Upon receiving one or both of these types of quarterly heatmaps, the doctor is dynamically informed how certain antibiotic candidates are more prevalent than other antibiotic candidates for treating a particular infection due to a resistant pathogen when compared to the antibiogram of the doctor's facility, such as a hospital or outpatient care facility.

Parameter 2: Relevant Antibiotic Use (for Example, Ordered, Filled, and/or Administered) in a Particular Doctor's Geographic Region and Facility Systems and methods of the present disclosure inform a medical entity, using dynamically-updated data, how much relevant antibiotic use there is in the entity's particular geographic region and the entity's particular facility that treat the specific pathogen identified in Parameter 1 above. It will be understood that information on relevant antibiotic use can include information on antibiotics that have been ordered, filled, and/or administered in the entity's geographic region or facility. In one non-limiting example, embodiments of the present disclosure inform the doctor of studies that have evaluated the correlation of antibiotics used to treat the specifically-identified resistance type. For example, in the case of Carb NS/CRE, systems and methods described herein display studies that have evaluated the correlation of newer antibiotics to treat Carb NS/CRE, for example, Xerava, Vabomere, Avycaz, Zemdri, Zerbaxa, and colistin. Systems and methods of the present disclosure can evaluate and display other relevant information, such as but not limited to likely or prevalent complications associated with relevant antibiotic use in the particular doctor's geographic region and facility. For example, the percentage of patients that were prescribed a colistin-based treatment regimen that developed kidney dysfunction can be provided as an insight to the doctor. As another non-limiting example, insights relating to antibiotic combination regimens can be provided to the doctor based on the antibiotic selected under Parameter 1 above.

Lastly, intent to treat speaks to patterns of physician prescribing, which can also vary by geographic region and local cultural practices. In addition, physician subspecialists can often "override" admitting or general physician orders. Therefore, ordered versus administered medication may differ in volume, magnitude, and quantity. Systems and methods using analytics of one or both of ordered and administered medication (or medications filled in the ambulatory setting) might be preferentially used in embodiments of the present disclosure, depending on the type and purpose of the analyses.

Insights relating to this parameter can be based on data collected over a timeframe of the doctor's choosing or a timeframe established by the doctor's facility, a regulatory agency, or any other entity. In one non-limiting example, the timeframe is the quarter ending on the date the doctor requested or received the dynamically-updated data. Other example timeframes include the prior day, the prior week, the prior two weeks, the prior month, the prior two months, the prior six months, and the prior year. It will be understood that any suitable timeframe can be implemented in embodiments of the present disclosure.

Parameter 3: How Often Antibiotic Use is Inappropriate in a Particular Doctor's Geographic Region and Facility Systems and methods of the present disclosure inform a medical entity, using dynamically-updated data, how often the antibiotic selected in Parameter 1 is inappropriately selected to treat resistant pathogens in the medical entity's geographic region and the medical entity's facility. In one non-limiting example, embodiments of the present disclosure dynamically inform the doctor of the ineffective empirical treatment (IET) rate in the most recent quarter overall and locally (in the doctor's geographic region and the doctor's facility) of the antibiotic selected under Parameter 1 above. In another non-limiting example, embodiments of the present disclosure dynamically inform the doctor of the ineffective empirical treatment (IET) rate in the most recent quarter overall and locally (in the doctor's geographic region and the doctor's facility) for common infections. Example common infections include but are not limited to SSSI, bacteremia, CAP, HCAP, HAP/VAP, urinary tract infection (UTI).

Insights relating to this parameter can be based on data collected over a timeframe of the doctor's choosing or a timeframe established by the doctor's facility, a regulatory agency, or any other entity. In one non-limiting example, the timeframe is the quarter ending on the date the doctor requested or received the dynamically-updated data. Other example timeframes include the prior day, the prior week, the prior two weeks, the prior month, the prior two months, the prior six months, and the prior year. It will be understood that any suitable timeframe can be implemented in embodiments of the present disclosure.

Parameter 4: Testing of Newer Antibiotics for Relevant Pathogens and Susceptibilities of the Newer Antibiotics in a Particular Doctor's Geographic Region and Facility Systems and methods of the present disclosure inform a medical entity, using dynamically-updated data, how often newer antibiotic treatment regimens available on the market are tested for the relevant pathogens identified in Parameters 2 and 3 above. The dynamically-updated data can include information on susceptibilities of the newer antibiotics in the entity's particular geographic region and the entity's particular facility. Advantageously, embodiments of the present disclosure can determine susceptibility rates using real-word data, what types of patient testing is being performed using real-world data, and if testing is being done in admissions that may require such testing.

In one non-limiting example, systems and methods of the present disclosure evaluate susceptibility rate and minimum inhibitory concentration (MIC) distribution for pathogens tested to particular antibiotics identified in Parameter 1 above, overall and by source. Examples of newer antibiotics that are not included in conventional microbiology panels for routine testing include Xerava, Vabomere, Avycaz, Zemdri, and/or Zerbaxa. In another non-limiting example, systems and methods of the present disclosure evaluate quarterly trends in testing of newer antibiotics. In still another example, systems and methods of the present disclosure evaluate national and local rates of testing of these selected antibiotics to overall and source-specific resistance rates associated with a particular resistance types. This information can include, for example, resistant rate heatmaps for particular resistance types. Embodiments of the present disclosure can evaluate these insights to support selection of candidate antibiotics identified in Parameter 1 above.

Insights relating to this parameter can be based on data collected over a timeframe of the doctor's choosing or a timeframe established by the doctor's facility, a regulatory agency, or any other entity. In one non-limiting example, the timeframe is the quarter ending on the date the doctor requested or received the dynamically-updated data. Other example timeframes include the prior day, the prior week, the prior two weeks, the prior month, the prior two months, the prior six months, and the prior year. It will be understood that any suitable timeframe can be implemented in embodiments of the present disclosure.

Parameter 5: Identification of Patient-Specific Risk Factors for Specific Infection and Resistance Types Systems and methods of the present disclosure inform a medical entity, using dynamically-updated data, of patient risk factors for specific infection and resistance types identified in Parameters 1 through 4 above. Implementations of the present disclosure can develop a risk score on a population of patients that allows the medical entity to discriminate specific pathogen types by infection (for example, SSI, CAP, HCAP). For example, the risk score can take into account risk factors associated with the particular resistance or pathogen type. In another example, the risk score can take into account mixed resistance or pathogen types associated with these risk factors. Implementations of the present disclosure can develop incremental models to guide the need for coverage for specific mixed resistance or pathogen types. The dynamically-updated data can include information on susceptibilities of the newer antibiotics in the entity's particular geographic region and the entity's particular facility. Advantageously, embodiments of the present disclosure can determine susceptibility rates using real-word data, what types of patient testing is being performed using real-world data, and if testing is being done in admissions that may require such testing.

Insights relating to this parameter can be based on data collected over a timeframe of the doctor's choosing or a timeframe established by the doctor's facility, a regulatory agency, or any other entity. In one non-limiting example, the timeframe is the quarter ending on the date the doctor requested or received the dynamically-updated data. Other example timeframes include the prior day, the prior week, the prior two weeks, the prior month, the prior two months, the prior six months, and the prior year. It will be understood that any suitable timeframe can be implemented in embodiments of the present disclosure.

FIG. 1A is a block or data flow diagram of an example method that provides dynamically-updated regional, facility, and patient specific insights and analytics for the above-described parameters according to an embodiment of the present disclosure. The flow chart for method 10 may be performed by any device described herein, for example a computing system 102 or a dynamic system 103 of a system 100, described in further detail below. In some embodiments, one or more of the steps/blocks of the method 10 may be eliminated or combined with another step/block, or additional steps/blocks may be added to the method 10.

At block 12, the method includes receiving an input from a user (such as but not limited to a doctor, hospital administrator, or other healthcare professional). For example, the user is a doctor evaluating a patient suffering from an illness caused by a pathogen. The input from the doctor may include a selection of a particular antibiotic the doctor is considering prescribing, and/or a pathogen the doctor suspects or has confirmed is causing the illness, such as a bacterial infection. In some embodiments, the user provides the input including both the pathogen and antibiotic (for example, when the doctor is treating or planning to treat the selected pathogen with the selected antibiotic). In some embodiments, the input includes the selected pathogen only (for example, when the doctor is unsure which antibiotic to use to treat the selected pathogen). In some embodiments, the input includes the selected antibiotic only (for example, when the doctor is unsure what specific pathogen is causing an infection, but has an idea of what antibiotic to use to generally treat the patient's symptoms).

Based on the selected antibiotic and/or pathogen, the method 10 moves to block 14 in which resistance rates affiliated with the selected antibiotic and/or pathogen are identified. For example, the method 10 identifies and obtains or reviews information (for example, one or more of studies, reports, cultures information, heatmaps, antibiograms, and so forth) from one or more databases (for example, second data store 108, described in more detail below). An example study is illustrated in FIG. 1B. In one non-limiting embodiment, the doctor can evaluate this study, and other applicable studies, to assess if resistance rates to the selected antibiotic and/or pathogen are high in the doctor's geographic area, such as Region 2, or the doctor's facility, such as an acute care facility in Region 2, in the most recent quarter. In the example study, the doctor can ascertain that Carb-NS *P. aeruginosa* has a significantly higher non-susceptibility rate (17.1%) in the doctor's geographic region, Region 2, than in Regions, 1, 3, and 4. The method 10 may obtain the information and store it locally, for example in a database of the system 100.

Figure 1C:
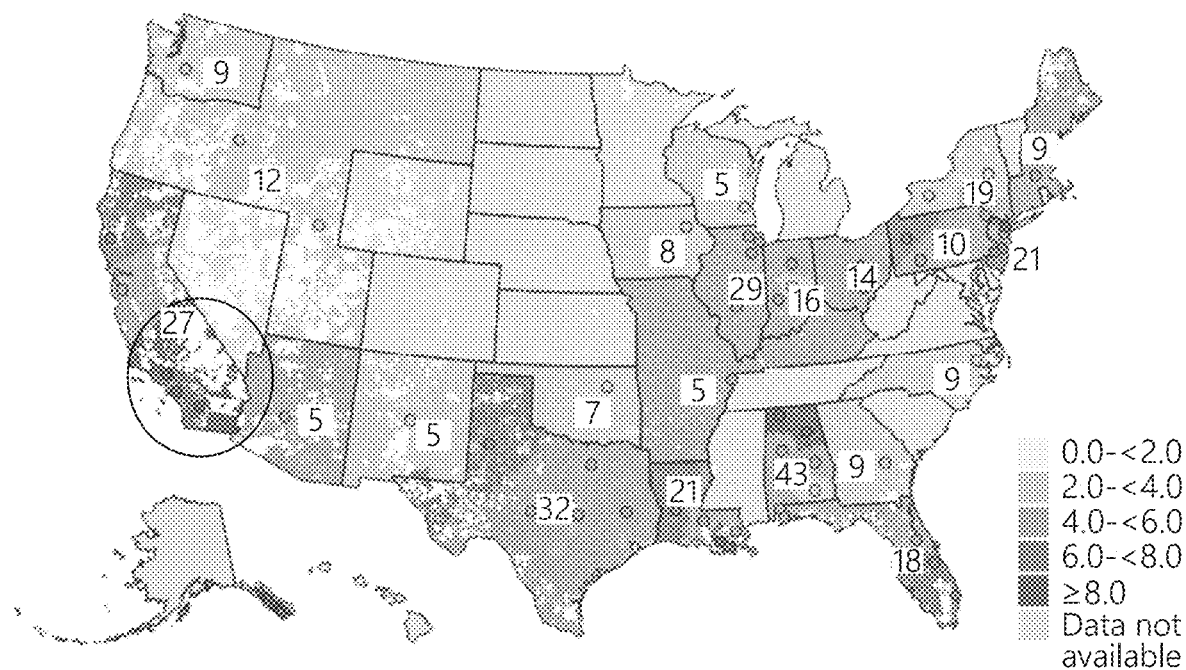

For example, based on the selected antibiotic, the method 10 obtains relevant heatmaps. An example heatmap is illustrated in FIG. 1C. This example heat illustrated the geographic incidence rate (per 1000 admissions) of urine isolates for a specific pathogen, Pathogen X, in hospitalized patients. An example pathogen is ESBL-ENT (extended-spectrum beta-lactamase Enterobacteriaceae). Using this heatmap, the doctor can assess that incidence rate for Pathogen X in urine isolates in the doctors particular geographic region, Southern California, is high relative to other geographic regions. Further details can be found in the description associated with parameter 1 above. Furthermore, the method 10 may obtain heatmaps related to the selected pathogen and/or the selected antibiotic. In another example, when the doctor provides both the selected antibiotic and the selected pathogen, the method 10 identifies heatmaps for the selected pathogen and the selected antibiotic, or just one or the other. The heatmaps may show drug resistance information for the selected antibiotic and/or the selected pathogen. For example, the heatmaps specific to the selected antibiotic show drug resistance in a particular geographic region or facility and during or over a particular time period for the selected antibiotic relative to pathogen commonly treated by the selected antibiotic. Heatmaps related to both the selected antibiotic and the selected pathogen may show drug resistance in a particular geographic region or facility and during or over a particular time period for the selected pathogen relative to the selected antibiotic (for example, as determined by urine, skin/wound, or respiratory cultures). In some embodiments, the user also selects the particular geographic region or facility and/or the particular time period as inputs to the system 100. In some embodiments, the particular geographic region or facility and/or the particular time period are predetermined. The predetermination may be a static predetermination based on, for example, the user's location, the facility, or a parameter detectable by the system. The predetermination may be a dynamic predetermination based on one or more parameters detectable by the system. For example, if the user is a mobile clinic user, the system may identify a geographic area within a threshold distance (e.g., within 50 or 100 miles) from the current location of a mobile device used by the mobile clinical user. Based on the obtained information, the method 10 may determine how a selected antibiotic candidate is more or less prevalent for treating the selected pathogen, considering any drug resistance features of the selected pathogen. In some embodiments, at block 14, the method 10 also identifies a particular resistance type based on the selected antibiotic and/or pathogen.

Once the various data is obtained at block 14, the method 10 may identify relevant antibiotic use for treating drug-resistant pathogens at block 16. In some embodiments, if the user selects the pathogen and the selected pathogen is not drug-resistant, then this step/block of the method 10 can be omitted or bypassed (by the system 100 or by selection of the user). In some embodiments, the selected pathogen is drug resistant and the system 100 identifies relevant use of antibiotics to treat the selected pathogens. The identified antibiotics may include the selected antibiotic or antibiotics commonly used to treat the selected, drug-resistant pathogen. Block 16 may include obtaining information, for example, studies specific to the selected antibiotics or to antibiotics commonly used to treat the selected pathogens that are drug resistant. In some embodiments, the obtained information further includes information regarding complications or side effects of particular antibiotics, treatment regimens that include multiple antibiotics, and so forth. Further details regarding block 16 can be found in the description associated with parameter 2 above. The obtained information may be relative to a particular geographic region or facility and during or over a particular time period for the selected pathogen relative to the selected antibiotic (for example, as determined by urine, skin/wound, or respiratory cultures). In some embodiments, the user also selects the particular geographic region or facility and/or the particular time period as inputs to the method 10. In some embodiments, the particular geographic region or facility and/or the particular time period are predetermined. The predetermination may be a static predetermination based on, for example, the user's location, the facility, or a parameter detectable by the system. The predetermination may be a dynamic predetermination based on one or more parameters detectable by the system. For example, if the user is a mobile clinic user, the system may identify a geographic area within a threshold distance (e.g., within 50 or 100 miles) from the current location of a mobile device used by the mobile clinical user.

Figure 1D:
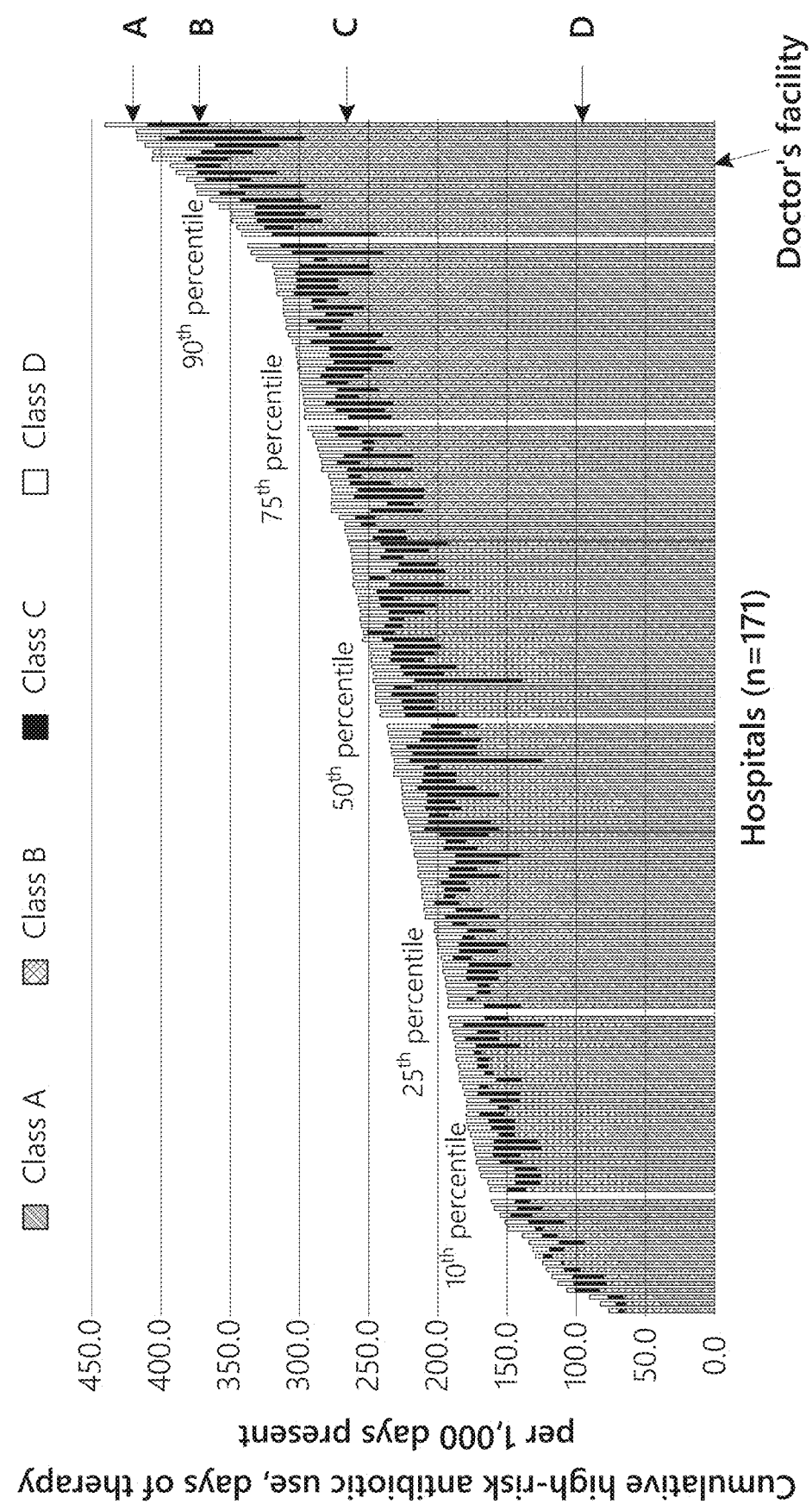

An example study is illustrated in FIG. 1D. In one non-limiting embodiment, the doctor can evaluate this study to assess how much relevant antibiotic use is occurring in the doctor's geographic region and/or the doctor's facility that treats specific resistant pathogens identified in block 12. Using the study illustrated in FIG. 1D, for example, the doctor can assess cumulative high-risk antibiotic use (sorted by overall high-risk antibiotic use rate) for 4 classes of antibiotics, Class A, Class B, Class C, and Class D. Example classes of antibiotic include cephalosporins, fluoroquinolones, carbapenems, and lincosamides. The doctor can determine, for example, that cumulative antibiotic use of Class D antibiotics is particularly high in the doctor's hospital.

At block 18, the method 10 determines details of relevant inappropriate antibiotic use to treat drug-resistant pathogens and uses this information to inform the user how often the selected antibiotic (or another antibiotic) is inappropriately selected to treat the selected pathogen. For example, the method 10 obtains information (for example, from one or more databases) related to effective treatment rates. For example, the method 10 identifies and/or receives the effective treatment rates (during the particular time period and in the particular geographic region or facility) for the selected antibiotic against the selected drug-resistant pathogen. Alternatively, or additionally, the method 10 identifies and/or receives the effective treatment rates for the selected antibiotic against common drug-resistant pathogens to which the antibiotic is generally applied. Alternatively, or additionally, the method 10 identifies and/or receives the effective treatment rates for one or more antibiotics commonly used against the selected drug-resistant pathogens. Further details regarding block 18 can be found in the description associated with parameter 3 above. The obtained information may be relative to a particular geographic region or facility, and during or over a particular time period for the selected pathogen relative to the selected antibiotic. In some embodiments, the user also selects the particular geographic region or facility and/or the particular time period as inputs to the system 100. In some embodiments, the particular geographic region or facility and/or the particular time period are predetermined. The predetermination may be a static predetermination based on, for example, the user's location, the facility, or a parameter detectable by the system. The predetermination may be a dynamic predetermination based on one or more parameters detectable by the system. For example, if the user is a mobile clinic user, the system may identify a geographic area within a threshold distance (e.g., within 50 or 100 miles) from the current location of a mobile device used by the mobile clinical user.

Example studies are illustrated in FIGS. 1E, 1F, and 1G. In one non-limiting example, the doctor can assess how often antibiotic use is inappropriate in the doctor's geographic region and/or facility for specific infection/resistance types. For example, the doctor can evaluate appropriate and inappropriate antibiotic use presented in FIG. 1E (initial empiric antibiotic therapy for complicated urinary tract infections (cUTI) for Pathogen Y) and FIG. 1F (clinical features of patients with cUTI caused by Pathogen Y). An example pathogen includes enterobacteriaceae. In another non-limiting example illustrated in FIG. 1G, the doctor can evaluate inappropriate empiric therapy (IET) by pathogen category for Antibiotic A through Antibiotic S. Example antibiotics include Vancomycin-IV, Piperacillin/Tazobactam-IV, Clindamycin-IV, Cefepime-IV, Ceftriaxone-IV, Meropenem-IV, Levofloxacin-IV, Cefazolin-IV, Ampicillin/Sulbactam-IV, Daptomycin-IV, Linezolid-IV, Ciprofloxacin-IV, Ceftaroline-IV, Sulfamethoxazole/Trimethoprim-ORAL, Ertapenem-IV, Doxycycline-ORAL, Ciprofloxacin-ORAL, Metronidazole-IV, and Levofloxacin-ORAL.

At block 20, the method 10 may identify one or more antibiotics available to treat the selected pathogen or to replace the selected antibiotic, or both. In some embodiments, such identifying includes receiving and/or parsing information related to the available antibiotics. For example, the method 10 may receive and evaluate susceptibility rates between pathogens (such as the selected pathogen or related drug-resistant pathogens) and antibiotics (such as the selected antibiotic, or antibiotics commonly used to treat the selected pathogen or related drug-resistant pathogens). In some embodiments, the information relates to testing of new antibiotics or trends in and/or rates of testing (for example, are new treatment regimens being tested). Further details regarding block 20 can be found in the description associated with parameter 4 above. The obtained information may be relative to a particular geographic region or facility and during or over a particular time period for the selected pathogen relative to the selected antibiotic. In some embodiments, the user also selects the particular geographic region or facility and/or the particular time period as inputs to the system 100. In some embodiments, the particular geographic region or facility and/or the particular time period are predetermined. The predetermination may be a static predetermination based on, for example, the user's location, the facility, or a parameter detectable by the system. The predetermination may be a dynamic predetermination based on one or more parameters detectable by the system. For example, if the user is a mobile clinic user, the system may identify a geographic area within a threshold distance (e.g., within 50 or 100 miles) from the current location of a mobile device used by the mobile clinical user.

An example study is illustrated in FIG. 1H. In one non-limiting embodiment, the doctor can evaluate this study to assess how often newer antibiotics available on the market are tested for the pathogen selected in block 12. Using the study illustrated in FIG. 1H, for example, the doctor can evaluate the source distribution for non-duplicate PSA (*Pseudomonas aeruginosa*) isolates tested to a newer antibiotic, in this case UT (Ceftolozane/Tazobactam).

At block 22, the method 10 may identify patient risk factors related to the selected pathogen and/or antibiotic or a determined specific infection type. In some embodiments, the patent risk factors include a risk score, for example for a population of patients. The risk factors may allow for identification or parsing by pathogen types or resistance types, or identification of pathogen types or resistance types based on the risk factors. For example, the method 10 may use the risk factors to identify particular a particular resistance or pathogen type (or mixed resistance or pathogen type) having particular (for example, user selected or predetermined) risk factors. Additionally, the method 10 may generate one or more models (for example, dynamic models) to identify particular mixed resistance or pathogen types and/or a particular antibiotic for use against the selected pathogen. Further details regarding block 22 can be found in the description associated with parameter 5 above. The obtained information may be relative to a particular geographic region or facility and during or over a particular time period, for the selected pathogen relative to the selected antibiotic. In some embodiments, the user also selects the particular geographic region or facility and/or the particular time period or as inputs to the system 100. In some embodiments, the particular geographic region or facility and/or the particular time period are predetermined. The predetermination may be a static predetermination based on, for example, the user's location, the facility, or a parameter detectable by the system. The predetermination may be a dynamic predetermination based on one or more parameters detectable by the system. For example, if the user is a mobile clinic user, the system may identify a geographic area within a threshold distance (e.g., within 50 or 100 miles) from the current location of a mobile device used by the mobile clinical user.

An example study is illustrated in FIG. 1I. In one non-limiting embodiment, the doctor can evaluate this study and related studies to identify patient risk factors for specific infection types (for example, skin and skin structure infections (SSSI), urinary tract infection (UTI), pneumonia bacteremia, CAP, HCAP, HAP/VAP) for the pathogen selected in block 12. Using the study illustrated in FIG. 1I, for example, the doctor can evaluate anti-pseudomonal beta-lactams prescribed as empiric therapy in post-index *Pseudomonas aeruginosa* (PSA) admissions by index PSA infection non-susceptibility (NS) status. Example antibiotics include antipseudomonal beta-lactam, carbapenem (Carb), extended-spectrum cephalosporins (ESC2), and piperacillin/tazobactam (TZP).

In some embodiments, the method 10 generates a customizable output to the user at block 24. In some embodiments, the output to the user is an interactive report or notification, for example providing the user with the various information obtained by the method 10 as described with respect to FIG. 1A and the parameters described above. The report generated by the method 10 may include, for example, the selected antibiotic (or a replacement antibiotic when a more effective replacement is identified by the method 10 for use against the selected pathogen). In some embodiments, the report includes the obtained heatmaps, reports, and other relevant information. Thus, the block 24 may generate an output relative to the processing of the method 10 and based on the outputs of the various blocks and parameters, relative to the discussion above.

In some embodiments, the user may interact with the method 10 through a user interface. As such, the user may have an option to select which steps of the method 10 to perform based on inputs provided to the system 100 implementing the method 10. For example, the user may choose to skip identification of new antibiotics if the user has confirmed that a particular antibiotic will be used in a treatment regimen.

Example Database System to Provide Dynamically-Updated Parameters

Embodiments of the present disclosure can include a database system (also herein referred to as "the system") for integrating data from remote, possibly disparate database systems and dynamically generating electronic notifications (also referred to herein as "notifications" or "alerts") to various medical entities, for example using one or more customized models to provide dynamically-updated data relating to any one or a combination of Parameters 1 through 5 above. Subsets of the data from the disparate database systems may be processed and merged and further filtered to match the requirements and criteria selected by a medical entity. In addition, various filters, including geographic filters, facility-type filters, treatment regimen filters, pathogen filters, resistance type filters, and/or infection type filters may also be applied to aggregate and/or parse the merged subsets of data into data sets which can be used to dynamically generate the electronic notifications without straining available processing power or memory storage, which may occur when datasets are used at too granular a level. The aggregation of the merged subsets of data may also assist with improving accuracy levels which can also decline when large numbers of datasets are merged.

Embodiments of the present disclosure may also allow the system and/or method to conduct such processing, merging, filtering, aggregation, and/or alerting in a time efficient manner while data is added to the database and/or the individual entity requests (selected filters, etc.) may be different.

The system and method may rely upon data feeds from a plurality of databases, where one or more databases of the plurality of databases include data in different formats and/or relating to different information and/or geographic regions. The dynamically-generated, customized alerts may be generated based on various customized models and rules for processing data and generating outputs based thereon. Processing the data may include, for example, aggregating, filtering, merging, comparing, and/or refining the data in the databases as well as the automatic generation of new data files and/or databases.

Terms

In order to facilitate an understanding of the systems and methods discussed herein, a number of terms are described below. The terms described below, as well as other terms used herein, should be construed broadly to include the described information, the ordinary and customary meaning of the terms, and/or any other implied meaning for the respective terms. Thus, the descriptions below do not limit the meaning of these terms, but only provide exemplary descriptions.

Data Store: Includes any computer readable storage medium and/or device (or collection of data storage mediums and/or devices). Examples of data stores include, but are not limited to, optical disks (for example, CD-ROM and DVD-ROM), magnetic disks (for example, hard disks, floppy disks, and so forth), and memory circuits (for example, solid state drives and random-access memory ("RAM")). Another example of a data store is a hosted storage environment that includes a collection of physical data storage devices that may be remotely accessible and may be rapidly provisioned as needed (commonly referred to as "cloud" storage).

Database: Includes any data structure (and/or combinations of multiple data structures) for storing and/or organizing data, including, but not limited to, relational databases (for example, Oracle databases and MySQL databases), non-relational databases (for example, NoSQL databases), in-memory databases, spreadsheets, as comma separated values ("CSV") files, eXtendible markup language ("XML") files, TeXT ("TXT") files, flat files, spreadsheet files, and/or any other widely used or proprietary format for data storage. Databases are typically stored in one or more data stores. Accordingly, each database referred to herein (for example, in the description herein and/or the figures of the present application) is to be understood as being stored in one or more data stores.

Database Record and/or Record: Includes one or more related data items stored in a database. The one or more related data items making up a record may be related in the database by a common key value and/or common index value, for example.

Electronic Notification, Notification, and/or Alert: Includes electronic notifications of a result of a computation, analysis, and/or other processing of records. Notifications may indicate, for example, to a user (such as a medical entity), the result of the computation, analysis, and/or other processing of records. Notifications may be transmitted electronically, and may cause activation of one or more processes, as described herein.

User and/or Medical Entity: Includes an entity that provides input (for example, a request) to the system and/or an entity that utilizes a device to receive the event notification, notification or alert (for example, a user who is interested in receiving notifications). Non-limiting examples of users include physicians, nurses, pharmacists, medical staff, medical administrators, medical researchers, and regulatory agencies.

Example Operation of a Dynamic System According to the Present Disclosure

Figure 2:
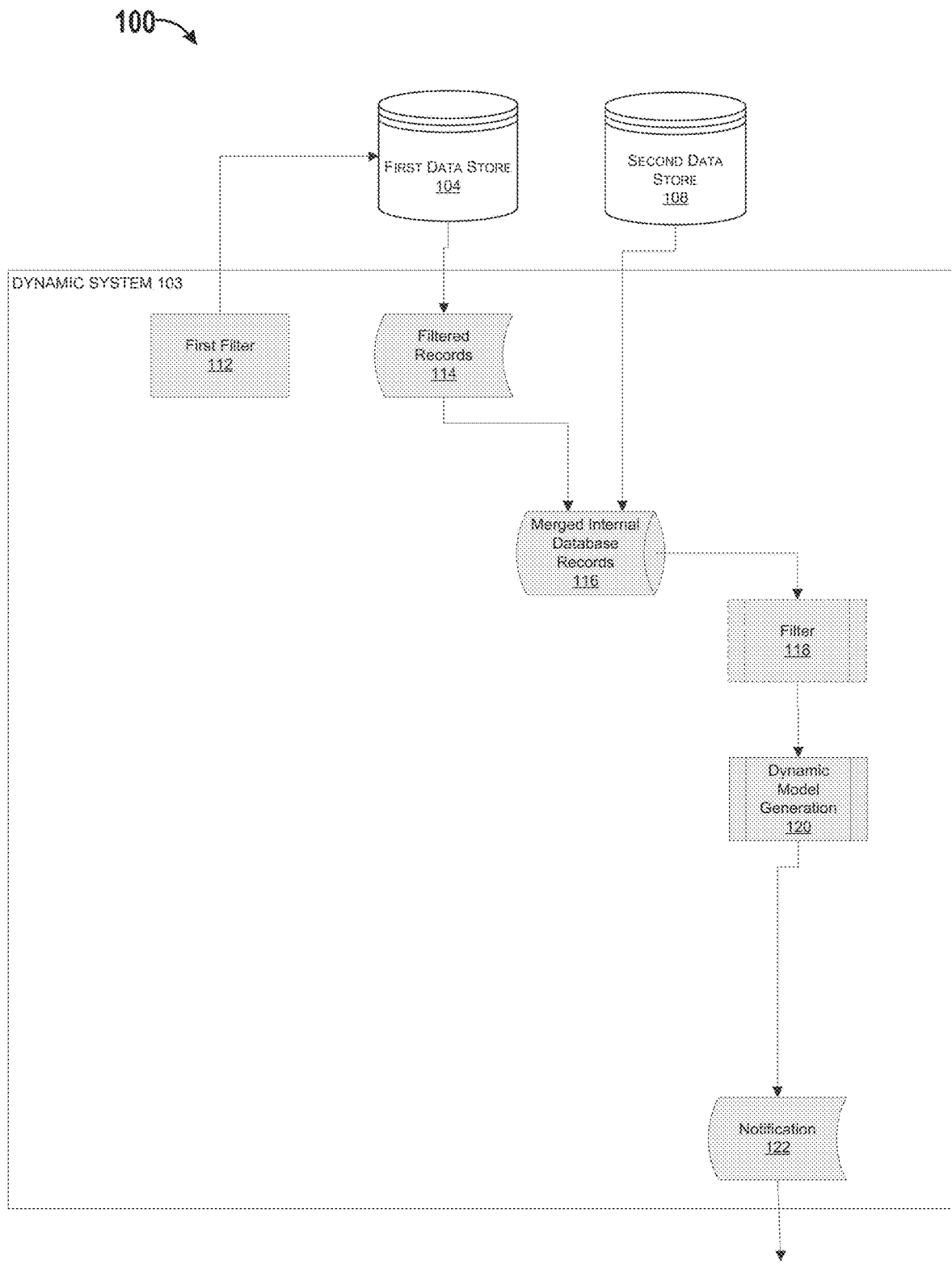
FIG. 2 illustrates an example of a block or data flow diagram of a treatment regimen database system, referred to as a dynamic system, according to one embodiment of the present disclosure.

FIG. 2 illustrates an example block or data flow diagram of a treatment regimen database system, referred to as a dynamic system 103 or the system 103, according to one embodiment of the present disclosure. The system 103 uses database records in various databases to dynamically generate electronic notifications, for example regarding treatment regimen efficacy rates, antibiotic usage and infection rates by geographic region and facility, resistance heatmaps, and other information relating to Parameters 1 through 5 described above. In some implementations, one or more of the blocks of FIG. 1A may be optional, additional blocks may be added, and/or blocks may be rearranged. As shown, the system 103 is part of a system 100, which is described in further detail with respect to FIG. 5.

The system 103 includes first filter 112 information, filtered records 114, merged internal database records 116, a filter 118, a dynamic model 120, and a generated notification. First filter 112 is configured to filter records in a first data store 104. In some embodiments, the first data store 104 stores information about a patient population. The first filter 112 may include content selected by the user (for example, a selected antibiotic and/or selected pathogen). The dynamic system 103 may use first filter 112 to identify a number of the records in the first data store 104 that meet, match, or otherwise are based on the filter content and filter execute calculations on specific subsets of the patient population. A database record in the first data store 104 may represent a patient, and may include the patient's name, address (including city, county, state, country, and zip code), previous medical history, prior treatment regimens (including information on effectiveness of prior treatment regimens), current medical condition including suspected or confirmed infection, known health concerns or medical conditions, and currently-prescribed treatment regimens. In some embodiments, the first filter 112 includes instructions for applying or performing one or more specific filtering functions or calculations on database records stored by the system in the first data store 104. The system 103 may query the first data store 104 for specific sets of data and perform calculations on the data (based on the first filter 112) to automatically generate a set of filtered records 114. Non-limiting examples of such instructions and/or filters and/or calculations are described below. The system may determine that the first filter 112 includes instructions to perform a count of the number of people having records in the first data store 104 that reside within a specific geographic area, such as, for example, an identified geographic area, zip code, zip code+4 area, city, county, state, set of 5 specific zip codes, or any other suitable geographic region.

For example, the first filter 112 may be applied to records in the first data store 104 to generate or identify those records of the first data store 104 relating to or remaining after application of the first filter 112. In one non-limiting embodiment, the first data store 104 includes medical records for patients that have been admitted to or treated at a particular care facility (such as a specific hospital or outpatient facility) or that reside in a particular geographic region, for example a county or a state. Continuing with this non-limiting example, the first filter 112 may include one or more of a particular infection, a particular infection-causing pathogen, particular strains of an infection-causing pathogen, a treatment regimen (including type and dosage information of medication such as an antibiotic) prescribed to one or more patients, or a particular city in the state. By applying the first filter 112 to the records in the first data store 104, the dynamic system 103 generates a first set of filtered records 114 that includes only those records from the first data store 104 that match the user-selected parameters for the first filter 112. Thus, when the first data store 104 includes all patient records for a particular state and the first filter 112 includes a filter for Methicillin-Resistant *Staphylococcus Aureus* (MRSA) infections, the resulting filtered records 114 include only those records from the first data store 104 that involve patients who are or were infected with MRSA in the particular state.

In some embodiments, the second data store 108 may include records regarding efficacy rates of treatment regimens against particular infections or infection-causing pathogens. In some embodiments, the records may include details for particular geographic regions, different infection strains, different categories of patients, different treatment regimens, and so forth.

The filtered records 114, as described above, include those records from the first data store 104 that satisfy the first filter 112. In some embodiments, the dynamic system 103 combines the treatment regimen efficacy data from the second data store 108 with the filter records 114 to generate combined or merged internal database records 116. Such a combination of records may include the filtered records 114 further appended with the efficacy information from the second data store 108. Thus, the records in the merged internal database records 116 may include, for each patient record in the merged internal database records 116, details for each patient, including that patient's current infection(s) and current treatment regimen(s) (among other information) as appended with the efficacy information from the second data store 108. The details for each patient can also include information on that patient's previous infection(s) and previous treatment regimens to treat those previous infections. In one non-limiting example, the patient record for a patient infected with MRSA that indicates treatment with trimethoprim-sulfamethoxazole (TMP-SMX) is appended with the established efficacy rate for TMP-SMX against MRSA using information that was dynamically updated based on real-world data aggregated over the last quarter. In embodiments of the present disclosure, the appended information is specific for the geographic region in which the patient lives or was infected, and/or specific for the facility in which the patient is being treated.

In some embodiments, the merged internal database records 116 includes one or more (or all) items included in the corresponding database record of the first data store 104 with the appended information from the second data store 108. The dynamic system 103 may append the filtered records 114 with the information from the second data store 108 dynamically (for example, as new data or records are received in either the first data store 104 or the second data store 108, or at regular intervals, for example, on daily, weekly, monthly, bi-monthly, bi-annually, annually, every 28 days, or on any other suitable schedule). In some embodiments, the dynamic system 103 may filter and merge the records from the first data store 104 and the second data store 108 when information is requested by a user of the dynamic system 103.

Advantageously, storing such filtered records and merging the filtered records with efficacy information can speed up later processing by the dynamic system 103, such as, for example, the dynamic generation of custom models, and/or additional filtering or merging operations. For example, as described below, by storing a subset of patient records associated with a treatment regimen or an infection, such as those patients infected by MRSA and treated with intravenous vancomycin, in real-time or on a periodic basis, those records can be more quickly analyzed and merged with other data sets that are organized at one or more levels when the system receives a user request. Indexing is one way data may be accessed more quickly. Factors that impact the indexing process and resources needed to index include the number of records being indexed, the number of fields included in the index, and the size of the data stored in the fields included in the index. The subset of information can be specifically indexed to expedite future retrieval and analysis of the records while using a resource efficient index.

In some embodiments, one or more of the first data store 104 and the second data store 108 may be updated, for example, on daily, weekly, monthly, bi-monthly, bi-annually, annually, every 28 days, or on any other type of schedule. In some embodiments, the first data store and/or the second data store 108 may be updated on demand or whenever a specific threshold of change has been detected (for example, 2% of the records have been updated, 0.8% of certain fields of the records have been updated, and so forth).

In some embodiments, the merged internal database records 116 are stored in a separate file from either the first data store 104 and/or the second data store 108, whereas in other embodiments, the merged internal database records 116 are stored in one of the first data store 104 and the second data store 108. In some embodiments, there may be some advantages to storing the merged internal database records 116 separately, such as for example, when the accessed set of data is a smaller data set in comparison to the complete set of records in the first data store 104 and/or the second data store 108 or, as another example, when the merged internal database records 116 are stored as a file or in a system that can be more readily read and accessed than the first data store 104 and/or the second data store 108. In some embodiments, the merged internal database records 116 are stored locally within the dynamic system 103, whereas in other embodiments, the merged internal database records 116 are stored remotely from the dynamic system 103, such as in an external database or in the second data store 108. If separate from the second data store 108, the merged internal database records 116 may be processed by the dynamic system 103 without having to further communicate with the first data store 104 or the second data store 108 to process the merged internal database records 116.

In the next step of this example process, the dynamic system 103 may then apply a filter 118 to the merged internal database records 116. This may occur in real-time or on a periodic basis, as explained above. In some embodiments, the filter 118 includes one or more criteria which is stored in the dynamic system 103 or accessed by the dynamic system 103. The filter 118 may be used to focus insights on a particular treatment regimen, infection, geographic region, and so forth. In some embodiments, a subset of data generated from applying the filter 118 is stored as a separate database from the merged internal database records 116, whereas in other embodiments, the filtered subset of the data is stored in a temporary memory location, such as RAM or buffer memory to be accessed for use in a dynamic model 120, discussed in detail below.

In some embodiments, when the filter 118 is applied, one or more criteria of the filter 118 are based on user-inputs. For example, a user may utilize a computing device to interface with the dynamic system 103 and request information on an efficacy of a specific treatment regimen against a particular infection or a particular pathogen within a specific geographic region. It will be understood that, in some cases, a particular infection or pathogen has not yet been conclusively identified, and the insights may be provided to the user based on symptoms experienced by a patient. In some embodiments, additional information, such as dates of interest, are provided by the user as data parameters. For example, the user may also provide instruction to filter results outside of a period of six months before a current date to ensure that the information used in the analysis and processing is timely and relevant.

In some embodiments, the dynamic system 103 (for example, via a dynamic model generator) may dynamically generate and apply the dynamic model 120 (for example, as a custom model or custom modeling algorithm) that groups the filtered subset after applying the filter 118 to determine a prediction or a likelihood estimation for an appropriate treatment regimen to treat a current infection. The dynamic system 103 may use the various forms of data described above to generate the dynamic model 120. Using the example above, the dynamic system 103 may take the filtered set of patient records for a specific infection or pathogen, a specific treatment regimen, and a specific geographic region, to dynamically generate the dynamic model 120 that determines the treatment regimen with the highest efficacy rate (or a higher efficacy rate than other candidate treatment regimens) to treat a current infection by optimizing the likelihood of the selected treatment regimen has a highest (or sufficiently high) efficacy against the infection in question in a given time period, a given geographic region, and so forth. In some embodiments, the dynamic model 120 considers the different parameters 1-5 described above and generates the report that is output to the user, including the risk factors and/or the risk score. The dynamic model 120 may be dynamic in how the model itself is continuously updated with additional information that may affect output generated by the dynamic model 120.

In some embodiments, the dynamic system 103 may generate and/or identify efficacy rate thresholds used in generating recommendations. For example, when a treatment regimen has an efficacy rate that is less than a first threshold, then that particular treatment regimen may not be recommended by the system 100. In one non-limiting example, when a treatment regimen has an efficacy rate falling below a first threshold of 90%, that particular treatment regimen is not recommend by the system 100. Alternatively, or additionally, if the efficacy rate is above a second threshold, then a second (for example, newer) treatment regimen may be recommended over a first (older or previously selected) treatment regimen, even if the first treatment regimen has an acceptable efficacy rate (for example, that is above the first threshold). In one non-limiting example, if the efficacy rate is greater than a second threshold of 80%, then a second (for example, newer) treatment regimen is recommend over a first (older or previously selected) treatment regimen, even if the first treatment regimen has an efficacy rate over a first threshold of 90%. It will be understood that these example first and second thresholds are not limiting, and that embodiments of the present disclosure can be suitably implemented using other acceptable first and second thresholds.

For example, the user may seek insights and situation awareness on the optimal (most appropriate) treatment regimen to treat MRSA in a particular geographic region. The user may filter the patient records in the first data store 104 (for example, via the first filter 112, comprising the infection MRSA) to generate the filtered records 114 that include only those patient records for patients exposed to MRSA (in the user's specific geographic region, the specific geographic region in which the patient resides, the specific geographic region where the patient contracted the infection, the user's specific facility, or any combination of these) and the corresponding treatment regimens that were used to treat MRSA in those cases. The dynamic system 103 generates the merged internal database records 116 by applying efficacy rates from the second data store 108 to the filtered records 114. The dynamic system 103 may then further filter the merged internal database records 116 (for example, based on one or more of a geographic area, period of time of interest, and so forth). The resulting subset of records may then be used to generate a custom model that is used to identify the optimal (most appropriate) treatment regimen to treat the MRSA infection based on a current patient's medical information and the records in the subset of records, the merged internal database records 116, or the filtered records 114. As described above, embodiments of the present disclosure include the dynamic model(s) 120 that takes into account patient-specific information, such as but not limited to the specific patient's prior exposure to the same pathogen causing a current infection, the specific patient's prior infections that are confirmed or likely to have been caused by the same pathogen, and the specific patient's prior resistance to treatment of the same infection (using the same or different treatment regimens as those the user is currently considering to treat the current infection).

The dynamic modeling described herein (as performed by the dynamic model 120) may allow for updating of efficacy rate information for various treatment regimens and providing alerts or notifications for recommended treatment regimens in view of diagnosed infections without having to overtax the medical facility's computing systems. For example, embodiments of the present disclosure can avoid overtaxing a medical facility's computing system by focusing on, and delivering relevant insights for, parameters identified by the system (or a user of the system) rather than irrelevant parameters. For instance, insights for a particular geographic region or a particular time frame can be developed without the need to process data for other, irrelevant geographic regions or timeframes. As another example, embodiments of the present disclosure can avoid overtaxing a medical facility's computing system by dynamically generating patient and efficacy rate information based on data that is updated in real-time or near real-time, thereby reducing memory requirements of the computing system. As explained above, one or more of the first data store 104 and the second data store 108 can be updated as frequently as daily, weekly, or monthly, or on any other suitable schedule.

The dynamic system 103 may also generate an output file or notification 122 dynamically or on a periodic basis (for example daily, weekly, monthly, bimonthly, quarterly, semi-annually, and so forth), and send a notification alert or notification package. The generated notification package or alert may include a digital and/or electronic message. The notification package may include an indication of the user's selected treatment regimen to treat a patient's current infection. The notification package can include an indication that the user should access the dynamic system 103 to review the records from the various data stores and databases associated with the dynamic system 103. The notification may be sent to the user that provided the filter criteria, and/or to any other recipient indicated by the user or the notification package. Further, the notification package may be delivered by any appropriate mode. Using the example above, the dynamic system 103 may send a notification package that includes information regarding the optimal treatment regimen to treat an infection in a given geographic region based on efficacy data obtained over a defined time period.

In some embodiments, such notification alerts (referred to herein also as notifications 122) may include a notice recommending against prescribing a particular treatment regimen, along with a recommendation to prescribe an alternate treatment regimen. The dynamic modeling described herein may enable the dynamic system 103 to generate updated efficacy rates by monitoring and aggregating patient records and analyzing them to identify factors that cause the efficacy rates to increase or decrease. The dynamic modeling may consider various geographic factors, time periods, and the like to determine the updated efficacy rates.

In some embodiments, the alert and/or notification is automatically transmitted to a device operated by the user associated with the corresponding notification. The alert and/or notification can be, for example, transmitted at the time that the alert and/or notification is generated, or at some pre-determined time after generation of the alert and/or notification, to a computing device 106 described below with reference to FIG. 3 and FIG. 5. When received by the computing device 106, the alert and/or notification can cause the computing device 106 to display the alert and/or notification via the activation of an application on the computing device 106 (for example, a browser, a mobile application, and so forth). For example, receipt of the alert and/or notification may automatically activate an application on the computing device 106, such as a messaging application (including but not limited to an SMS or MMS messaging application), a standalone application (for example, a user's messaging application), or a browser, and display information included in the alert and/or notification. If the computing device 106 is offline when the alert and/or notification is transmitted, the application may be automatically activated when the computing device 106 is online such that the alert and/or notification is displayed. As another example, receipt of the alert and/or notification may cause a browser to open and be redirected to a login page generated by the system 100 so that the user can log in to the system 100 and view the alert and/or notification. Alternatively, the alert and/or notification may include a URL of a webpage (or other online information) associated with the alert and/or notification, such that when the computing device 106 receives the alert, a browser (or other application) is automatically activated and the URL included in the alert and/or notification is accessed via the Internet.

In some implementations, the alert and/or notification may be automatically routed directly to an interactive user interface where it may be viewed and/or evaluated by the user, for example the doctor or administrator. In another example, the alert and/or notification may be automatically routed directly to a printer device where it may be printed in a report for review by the user. In another example, the alert and/or notification may be automatically routed directly to an electronic work queue device such that information from the notification may automatically be displayed to a user, and optionally information from the notification may be automatically used, for example, to contact (for example, dial a phone number) entities (such as but not limited to supervisors or hospital administrators) represented in the notification. In a further example, the alert and/or notification may be automatically routed as input to an external system (for example, to be fed into a pharmacy's prescription management system, a hospital patient management system, or a health insurance customer relationship management system).

In some embodiments, the notification 122 may indicate or recommend to the doctor not to prescribe a treatment regimen initially selected by the doctor, if the infection the treatment regimen is being prescribed against is more drug resistant than a given threshold (for example, more than 50% resistant in a given geographic region, making the treatment regimen less than 50% effective). Alternatively, or additionally, if a different treatment regimen is more effective (meaning less drug resistant) than the selected treatment regimen, then the notification 122 may indicate a recommendation to the doctor to prescribe the more effective treatment regimen. For example, if the different treatment regimen has an efficacy rate of greater than a second threshold (for example, more than 70% effective against the infection in the given region or given facility), the notification 122 may recommend the different treatment regimen over the initially selected treatment regimen.

In various implementations, the first data store 104, the second data store 108, the filtered records 114, the merged internal database records 116 and/or any combination of these databases or other databases and/or data storage devices of the system may be combined and/or separated into additional and/or the subset of records generated after the filter 118 is applied may be merged into one or more common databases or separated into different databases.

Figure 3:
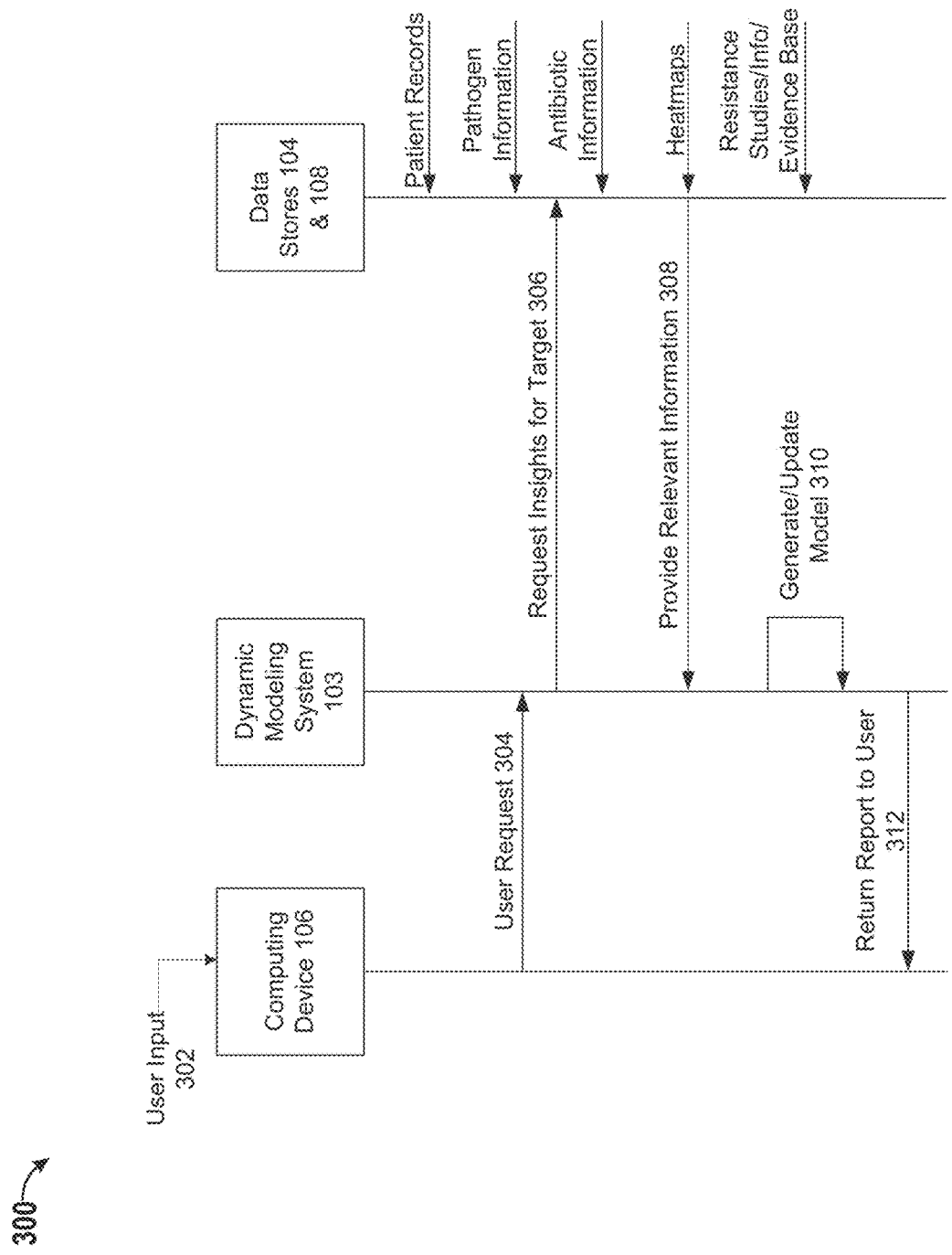
FIG. 3 is one embodiment of a communication flow diagram depicting communications passing between various components of the system of FIG. 2 for providing electronic notifications regarding database records, according to an embodiment.

FIG. 3 is an example communication flow diagram 300 depicting communications passing between various components of the system 100 of FIG. 2 for providing electronic notifications regarding database records, according to an embodiment of the present disclosure. The communication flow diagram 300 illustrates several components of the system 100. The communication flow of this non-limiting embodiment involves a computing device 106, the data stores 104 and 108, and the dynamic system 103. Though not shown, each of the computing device 106, the data stores 104 and 108, and the dynamic system 103 may be coupled via a network, such as the network 110 of FIG. 5 described in detail below. Accordingly, each of the depicted components may be configured to communicate over a network connection, for example.

In one embodiment, the computing device 106 is configured to receive a user input 302. The computing device 106 that receives the user input 302 may be a computing device 102, described below with reference to FIG. 5. In some embodiments, the user input 302 may be one or more of a selected antibiotic and a selected pathogen. Additionally, the user input 302 may include a geographic constraint and/or a time period or duration of interest. The user inputs 302 may all be provided at a single time or at different times or intervals. Similarly, the data stores 104 and 108 may be configured to receive or obtain various types of information, including patient information and/or health records, pathogen information (including resistance information, susceptibility information, and the like), antibiotic information (including resistance information, susceptibility information, testing information, and the like), heatmaps, and drug resistance studies. In some embodiments, the patient information and health records are stored in the first data store 104 and the remaining information is stored in the second data store 108.

Based on the received user input 302, the dynamic system 103 may generate a user request 304 to the dynamic system 103. The user request 304 to the dynamic system 103 may include one or more of the selected antibiotic, the selected pathogen, the particular geographic region, and the particular time period or frame. When the computing device 102 receives the user input 302, the computing device 102 may generate the user request 304 based on the received user input 302.

The dynamic system 103 may receive the user request 304 and generate one or more requests for insights for a target based on the user request 304. For example, the request for insights for the target may include a request for insights for a particular patient, a particular facility, and/or a particular geography. Additionally, or alternatively, the request for insights 306 can include a request for insights relative to the selected antibiotic and/or the selected pathogen over a particular time period or frame.

Based on the received request for insights 306, the data stores 104 and 108 may obtain and/or access data. For example, first and second data stores 104 and 108 may obtain or access patient records; pathogen information; antibiotics information; heatmaps; drug resistance studies, information, and evidence; and the like. The data stores 104 and 108 may provide the obtained or accessed data to the dynamic system 103 at 308. In some embodiments, the relevant information provided from the data stores 104 and 108 to the dynamic system 103 includes patient records or information from the patient records, the pathogen information (for example, details about the drug resistance of the pathogen, and similar information), details about the selected antibiotic, heatmaps (for example, those generated by the dynamic system 103 or the system 100 previously), and other relevant information. The dynamic system 103 may use the information from the user request 304 and the relevant information 308 to generate and/or update a dynamic model 310. The dynamic model 310 uses the user request 304 and the relevant information 308 to generate analysis or additional information regarding the best antibiotic and/or treatment regimen for treating the selected pathogen. In some embodiments, the best antibiotic may be the selected antibiotic or another antibiotic. The dynamic model 310 may parse the received request and relevant information 308 to identify information about the efficacy of the selected antibiotic against the selected pathogen, which may include drug resistance information.

After the dynamic model is generated or updated at 310, the dynamic system 103 may provide a report to the user at 312. In some embodiments, the report may include one or more pieces of information the dynamic system 103 used to generate a recommended antibiotic and/or treatment regimen as well as relevant risk factors (described in further detail herein). The report 312 may also include heatmaps, pathogen information, patient information, and other information from the data stores 104 and/or 108, as well as analysis generated by the dynamic system 103 relevant to the recommended antibiotic and/or treatment regimen and the corresponding selection. The report 312 may include all of this information to allow the user to review any information relevant to the recommendation.

Figure 4:
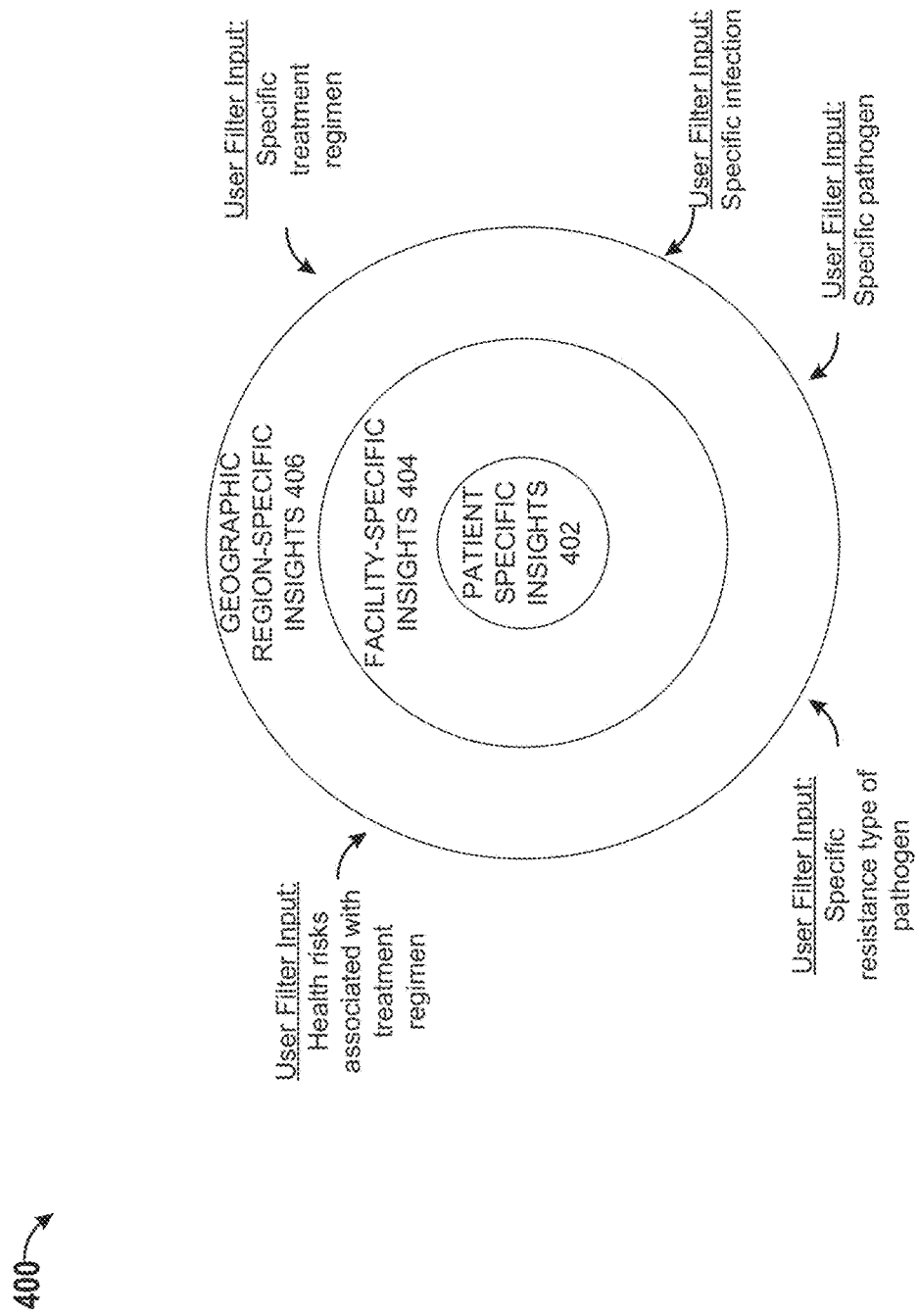
FIG. 4 illustrates a diagram of overlapping levels of insights available from the system of FIG. 2, according to an embodiment.

FIG. 4 illustrates a diagram 400 of overlapping levels of insights that are available to a user of the system 100 of FIG. 2, according to an embodiment of the present disclosure. For example, the diagram 400 shows multiple levels of insight that the system 100 can provide. The first level, the patient-specific insights level 402, may include insights specific to a particular patient. As such, based on various inputs (examples shown in FIG. 4), the system 100 may identify one or more particular patient insights based on the input, and deliver these insights to the user. In one non-limiting example, the system 100 can identify whether the specific patient being examined or reviewed is currently infected by or was previously infected by a specific pathogen. In another non-limiting example, the system 100 can identify whether the specific patient being examined or reviewed has health risks associated with a particular treatment regimen. In still another non-limiting example, the system 100 can identify whether the specific patient was previously treated or is currently treated using a specific treatment regimen. As described in detail above, the system 100 can advantageously deliver these and other insights to the user during an optimal window in the patient care timeline.

The second level, corresponding to the next largest circle in the diagram 400, represents facility-specific insights 404, representing insights for a particular facility. The facility-specific insights may include insights for patients treated at the particular facility. For example, the system 100 can identify patients being examined for, treated for, determined to be exposed to, etc., a specific pathogen. Thus, the facility-specific insights 404 for the particular facility inherently include patient specific insights 402 for patients treated at the particular facility.

The third level, corresponding to the next largest circle in the diagram 400, represents geography-specific insights 406, representing insights for a particular geographic region. The geography-specific insights may include facility-specific insights for facilities that exist within the particular geographic region. For example, the system 100 can identify all patients within the particular geographic region being examined for, treated for, determined to be exposed to, etc., a specific pathogen, which would include any particular patients treated at any particular facilities within the particular geographic region. Thus, the geography-specific insights 406 for the particular geographic region inherently include facility-specific insights 404 for any facilities within the particular geographic region and patient-specific insights 402 for patients treated at the facilities within the particular geographic region. As described above, these insights can be based on real-time or real-time data aggregated over specific time periods, including time periods ending on the date of a user's request for insights. Accordingly, embodiments of the systems and methods of the present disclosure can provide dynamic, real-time insights and situational awareness to clinical staff at three core levels: geographic region-specific insights and situational awareness, facility-specific insights and situational awareness, and patient-specific insights and situational awareness.

Figure 5:
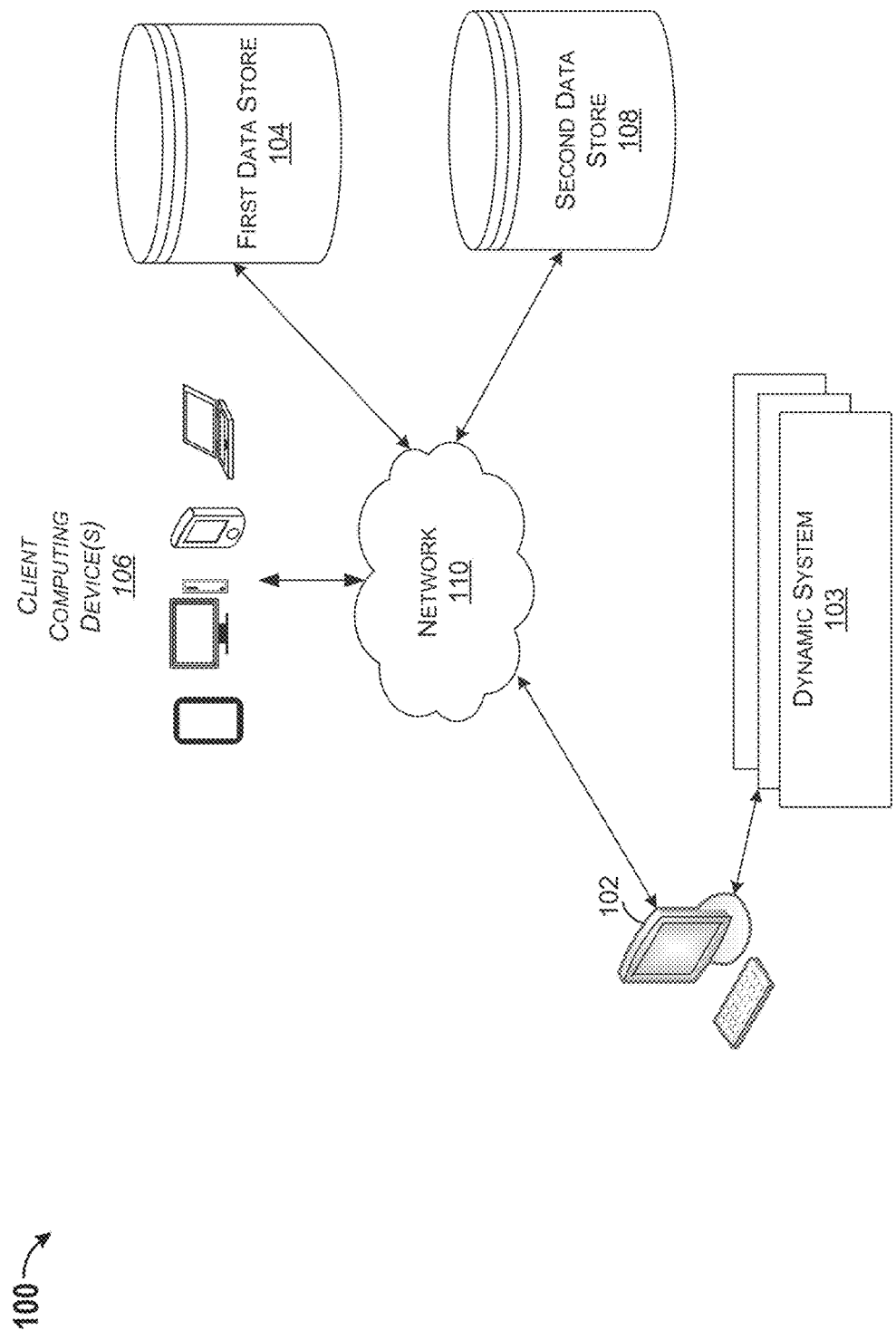
FIG. 5 illustrates a block diagram of one possible organization of the system of FIG. 2 that can dynamically generate and apply models for tracking medication efficacy and track situations for identifying potential drug resistance conditions based on information from one or more databases, according to an embodiment.
Figure 6:
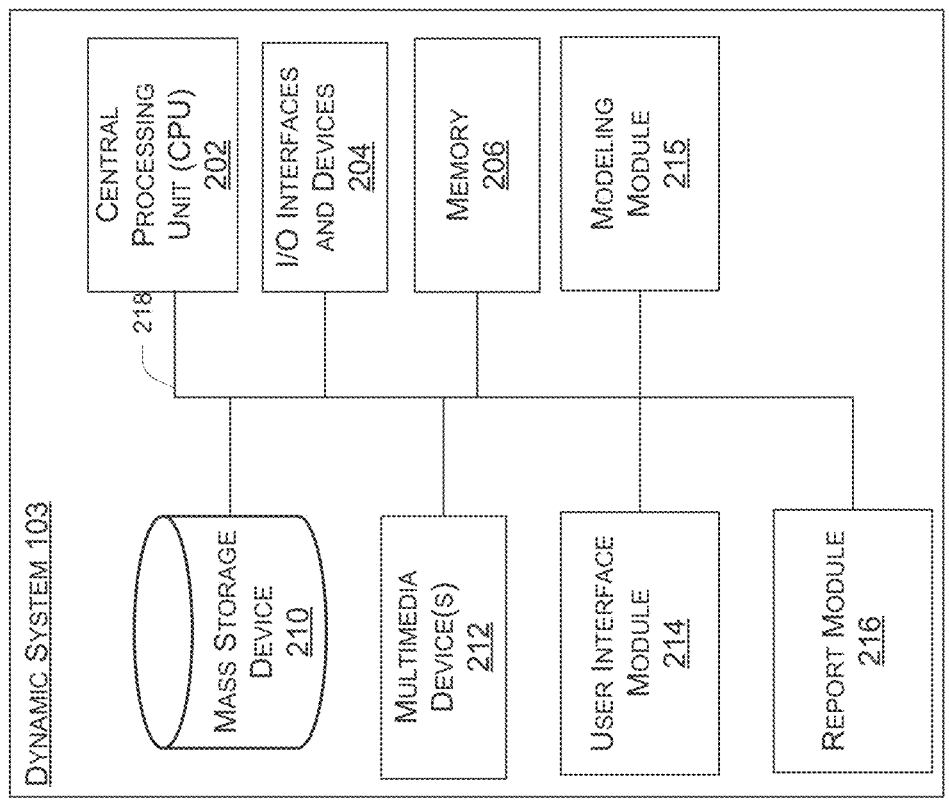
FIG. 6 is a block diagram corresponding to an aspect of a hardware and/or software component of an example embodiment of the dynamic system and/or the system of FIG. 2.

Additional Example Implementations of a Dynamic System According to the Present Disclosure FIGS. 5 and 6 illustrate additional non-limiting embodiments of a dynamic system 103 that is configured to communicate with data stores in a system 100 according to implementations of the present disclosure.

System Overview

FIG. 5 illustrates a block diagram of one possible organization of the system of FIG. 2 that can dynamically generate and apply models for tracking medication efficacy and track situations for identifying potential drug resistance conditions based on information from one or more databases, according to an embodiment of the present disclosure. The system 100 may allow users to dynamically generate models for processing records and data sourced from various databases where the models can generate outputs (for example, reports and notifications) from the data based on dynamically changing requirements from users.

The system 100 of FIG. 5 includes the dynamic system 103 interfacing with a computing device 102, the first data store 104, the second data store 108, additional computing devices 106, and a network 110. Additionally, communication links are shown enabling communication among the components of system 100 via the network 110. The computing device 102 is shown communicatively coupled to the dynamic system 103 in a localized manner (for example, via a local communication link), though the dynamic system 103 may be integrated into the computing device 102 or vice versa, or may be accessible via the network 110. Furthermore, in some embodiments, one or more of the data stores described herein may be combined into a single data store that is local to the computing device 102 or remote from the computing device 102. In some embodiments, two or more of the components described above may be integrated. In some embodiments, one or more of the components may be excluded from the communication system 100 or one or more components not shown in FIG. 5 may be included in the communication system 100. The communication system 100 may be used to implement systems and methods described herein.

In some embodiments, the network 110 may include any wired or wireless communication network by which data and/or information may be communicated between multiple electronic and/or computing devices. The wireless or wired communication network may be used to interconnect nearby devices or systems together, employing widely used networking protocols. The various aspects described herein may apply to any communication standard, such as a wireless 802.11 protocol. The computing device 102 may include any computing device configured to transmit and receive data and information via the network 110 for a medical entity. The medical entity may be an individual person (for example, an individual doctor or nurse), or an institution such as but not limited to a business, a non-profit organization, an educational institution, a medical facility. In some embodiments, the computing device 102 may include or have access to one or more databases (for example, the first data store 104 and the second data store 108) that include various records and information that may be used to generate customized outputs. In some embodiments, the computing device 102 may be accessible locally as well as remotely via the network 110. The computing device 102 may create the customized outputs based on events associated with a patient (for example, prior infections, prior prescribed treatment regimens, health events, and health risks). These events (and corresponding information) may be used to dynamically generate models for which treatment regimen to prescribe to ensure maximum efficacy against a particular infection, a particular pathogen, or a particular drug-resistant strain of a pathogen.

The first data store 104 may include one or more databases or data stores and may also store data regarding any of the historical or current events. Using the example use case, the first data store 104 may include patient records which include patient names, contact information, address information, medical information, current and past infections, prior treatment regimens prescribed, geographic regions in which the patient was infected (or was likely to be infected based on residence or travel information), and dates when the patient was ill. In some embodiments, the first data store 104 may provide data for patients within particular geographic regions, as defined by the user via the one or more computing devices 106 or the computing device 102. For example, the first data store 104 may provide details regarding patients in a geographic region defined by a state, county, zip code or other geographic identifier.

The computing devices 102, 106 may include any computing device configured to transmit and receive data and information via the network 110. In some embodiments, the computing device 106 may be configured to perform analysis of the transmitted and received data and information and/or perform one or more actions based on the performed analysis and/or the transmitted and received data and information. In some embodiments, the one or more computing devices 102, 106 may include mobile or stationary computing devices, including, but are not limited to, personal computers, server computers, hand-held or laptop devices, multiprocessor systems, microprocessor-based systems, a microcontroller or microcontroller based system, programmable consumer electronics, network PCs, minicomputers, mainframe computers, distributed computing environments that include any of the above systems or devices, and smartphones. As such, the users described herein (for example, the doctors, hospital administrators, and so forth) may use any of these types of devices to access the reports generated based on their request or inquiry. In some embodiments, the computing device 102, 106 may be integrated into a single terminal or device. In some embodiments, when the computing device 102 is remote from the patient, the user, a doctor, a hospital, and so forth. The computing devices 106 may be used by the users to access the network 110 and access the computing device 102 remotely. For example, the computing device 102 may be placed in the medical facility and accessible by the computing device 106.

The second data store 108 may also include one or more databases or data stores and may also store data regarding efficacy rates of treatment regimens against particular infections or pathogens, for example in different geographic regions and at during different defined timeframes. In the example use case, as described above, the second data store 108 includes a database of the efficacy rates for infections treated with treatment regimens corresponding to the infections and/or treatment regimens of the patients having records in the first data store 104.

The dynamic system 103 may process data from the first data store 104 and the second data store 108 and also generate one or more models based on requests or inputs provided by users via the computing devices 106 and the computing device 102. The dynamic system 103 may dynamically generate the one or more models that are applied to data obtained from one or more of the first data store 104, the second data store 108, or the users (via the one or more computing devices 106). In some embodiments, the models may be generated dynamically by the dynamic system 103 as the inputs and data change or on a predetermined schedule. For example, the dynamic system 103 may generate changing models in real-time based on the inputs received from the user (such as but not limited to types of infection being diagnosed, type of treatment regimens being prescribed, area where infection was contracted, and pertinent time frames). In some embodiments, the generated models themselves may be dynamically applied to the inputs and data. For example, the models generated by the dynamic system 103 may create various metrics and data points based on the data sourced from the first and second data stores 104 and 108, respectively, and data sourced from the users themselves (for example, the user's selected filters and geographic region). In some cases, the models may dynamically apply one or more rules to confirm that the outputs being generated do not violate any predetermined requirements or standards on data mining, storage, and so forth (for example, to ensure that medical information compliance factors are met). In some embodiments, the development of the model may include developing a set of heuristic rules, filters, and/or electronic data screens to determine and/or identify and/or predict which medications would be considered more likely to be meet specific criteria based on current and/or historical data. In some embodiments, the dynamic system 103 may automatically adjust the model to meet pre-selected levels of accuracy and/or efficiency.

In some embodiments, the dynamic system 103 may be adaptive to data from the first data store 104, the second data store 108, or from users that is constantly changing. For example, the inputs received from the user (for example, via a user interface module 214 or I/O interfaces and devices 204, described in further detail below) may be different for each user. Using the example use case, one user (for example, a first doctor) may be interested in efficacy rates for patients infected with MRSA when treated with TMP-SMX in a first set of zip codes, whereas another user (for example, a second doctor) may be interested in efficacy rates for patients infected with *Streptococcus Pneumoniae* when treated with penicillin in the first set of zip codes, whereas a third user (for example, a third doctor) may be interested in efficacy rates for a third infection when treated by a third medication. Accordingly, the data obtained from the first and second data stores 104 and 108, using the filter criteria from the users, will likely be constantly changing. Thus, the processing and/or model generation will change for each user and/or for each combination of data of interest. Additionally, the data obtained from the first and second data stores 104 and 108 will likely change over time as records in the data stores are updated, replaced, and/or deleted. In the example use case, different users may request different periods of time, different patient parameters, different infections, different treatment regimens, and so forth, such that the patient records and medication records are constantly updating. Accordingly, the dynamic system 103 may dynamically generate models to handle constantly changing data and requests.

Based on the user requests, as will be detailed herein, the data obtained from the first and second data stores 104 and 108, respectively, may be filtered to eliminate those records that are not desired. For example, in the example use case, records may be filtered to eliminate infections, dates, and/or treatment regimens not of interest.

In various embodiments, large amounts of data are automatically and dynamically calculated interactively in response to user inputs, and the calculated data is efficiently and compactly presented to a user by the system. Thus, in some embodiments, the data processing and generating of user interfaces described herein are more efficient as compared to previous data processing and user interfaces generation in which data and models are not dynamically updated and compactly and efficiently presented to the user in response to interactive inputs.

Further, as described herein, the system may be configured and/or designed to generate output data and/or information useable for rendering the various interactive user interfaces or reports as described. The output data may be used by the system 100, and/or another computer system, device, and/or software program (for example, a browser program), to render the interactive user interfaces or reports. The interactive user interfaces or reports may be displayed on, for example, electronic displays (including, for example, touch-enabled displays).

The various embodiments of interactive and dynamic data processing and output generation of the present disclosure are the result of significant research, development, improvement, iteration, and testing. This non-trivial development has resulted in the modeling and output generation described herein, which may provide significant efficiencies and advantages over previous systems. The interactive and dynamic modeling, user interfaces, and output generation include improved human-computer and computer-computer interactions that may provide reduced workloads, improved predictive analysis, and/or the like, for a user. For example, output generation via the interactive user interfaces described herein may provide an optimized display of time-varying report-related information and may enable a user to more quickly access, navigate, assess, and digest such information than previous systems.

In some embodiments, output data or reports may be presented in graphical representations, such as visual representations, such as charts, spreadsheets, and graphs, where appropriate, to allow the user to efficiently review the large amount of data and to take advantage of humans' particularly strong pattern recognition abilities related to visual stimuli. In some embodiments, the system may present aggregate quantities, such as totals, counts, and averages. The system may also utilize the information to interpolate or extrapolate, for example, forecast, future developments.

Further, the models, data processing, and interactive and dynamic user interfaces described herein are enabled by innovations in efficient data processing, modeling, interactions between the user interfaces, and underlying systems and components. For example, disclosed herein are improved methods of receiving user inputs, translation and delivery of those inputs to various system components, automatic and dynamic execution of complex processes in response to the input delivery, automatic data acquisition, automatic interaction among various components and processes of the system, and automatic and dynamic report generation and updating of the user interfaces.

Various embodiments of the present disclosure provide improvements to various technologies and technological fields. For example, as described above, existing data storage and processing technology (including, for example, in memory databases) is limited in various ways (for example, manual data review is slow, costly, and less detailed; data is too voluminous; and so forth), and various embodiments of the disclosure provide significant improvements over such technology. Additionally, various embodiments of the present disclosure are inextricably tied to computer technology. In particular, various embodiments rely on detection of user inputs via graphical user interfaces, acquisition of data based on those inputs, modeling of data to generate dynamic outputs based on those user inputs, automatic processing of related electronic data, and presentation of output information via interactive graphical user interfaces or reports. Such features and others (for example, processing and analysis of large amounts of electronic data) are intimately tied to, and enabled by, computer technology, and would not exist except for computer technology. For example, the interactions with data sources and displayed data described below in reference to various embodiments cannot reasonably be performed by humans alone, without the computer technology upon which they are implemented. Further, the implementation of the various embodiments of the present disclosure via computer technology enables many of the advantages described herein, including more efficient interaction with, and presentation of, various types of electronic data.

Example Dynamic System

FIG. 6 is a block diagram corresponding to an aspect of a hardware and/or software component of an example embodiment of the dynamic system 103 and/or the system 100 of FIG. 5. The hardware and/or software components, as discussed below with reference to the block diagram 200 may be included in any of the devices of the system 100 (for example, the computing device 102, the computing devices 106, or the dynamic system 103). These various depicted components may be used to implement the systems and methods described herein.

In some embodiments, certain modules described below, such as the modeling module 215, a user interface module 214, or a report module 216 included with the dynamic system 103 may be included with, performed by, or distributed among different and/or multiple devices of the system 100. For example, certain user interface functionality described herein may be performed by the user interface module 214 of various devices such as the computing device 102 and/or the one or more computing devices 106.

In some embodiments, the various modules described herein may be implemented by either hardware or software. In an embodiment, various software modules included in the dynamic system 103 may be stored on a component of the dynamic system 103 itself (for example, a local memory 206 or a mass storage device 210), or on computer readable storage media or other component separate from the dynamic system 103 and in communication with the dynamic system 103 via the network 110 or other appropriate means.

The dynamic system 103 may include, for example, a computer that is IBM, Macintosh, or Linux/Unix compatible or a server or workstation or a mobile computing device operating on any corresponding operating system. In some embodiments, the dynamic system 103 interfaces with a smart phone, a personal digital assistant, a kiosk, a tablet, a smart watch, a car console, an electronic assistant, a media player, or a similar electronic computing device. In some embodiments, the dynamic system 103 may include more than one of these devices. In some embodiments, the dynamic system 103 includes one or more central processing units ("CPUs" or processors) 202, I/O interfaces and devices 204, memory 206, a modeling module 215, a mass storage device 210, a multimedia device 212, the user interface module 214, a report module 216, and a bus 218.

The CPU 202 may control operation of the dynamic system 103. The CPU 202 may also be referred to as a processor. The processor 202 may include or be a component of a processing system implemented with one or more processors. The one or more processors may be implemented with any combination of general-purpose microprocessors, microcontrollers, digital signal processors ("DSPs"), field programmable gate array ("FPGAs"), programmable logic devices ("PLDs"), controllers, state machines, gated logic, discrete hardware components, dedicated hardware finite state machines, or any other suitable entities that can perform calculations or other manipulations of information.

The I/O interface 204 may include a keypad, a microphone, a touchpad, a speaker, and/or a display, or any other commonly available input/output ("I/O") devices and interfaces. The I/O interface 204 may include any element or component that conveys information to the user of the dynamic system 103 (for example, a requesting doctor, nurse, hospital administrator, researcher, or other entity) and/or receives input from the user. In one embodiment, the I/O interface 204 includes one or more display devices, such as a monitor, that allows the visual presentation of data to the consumer. More particularly, the display device provides for the presentation of GUIs, application software data, websites, web apps, and multimedia presentations, for example.

In some embodiments, the I/O interface 204 may provide a communication interface to various external devices. For example, the dynamic system 103 is electronically coupled to the network 110 (FIG. 5), which includes one or more of a LAN, WAN, and/or the Internet. Accordingly, the I/O interface 204 includes an interface allowing for communication with the network 110, for example, via a wired communication port, a wireless communication port, or combination thereof. The network 110 may allow various computing devices and/or other electronic devices to communicate with each other via wired or wireless communication links.

The memory 206, which includes one or both of read-only memory (ROM) and random access memory ("RAM"), may provide instructions and data to the processor 202. For example, data received via inputs received by one or more components of the dynamic system 103 may be stored in the memory 206. A portion of the memory 206 may also include non-volatile random access memory ("NVRAM"). The processor 202 typically performs logical and arithmetic operations based on program instructions stored within the memory 206. The instructions in the memory 206 may be executable to implement the methods described herein. In some embodiments, the memory 206 may be configured as a database and may store information that is received via the user interface module 214 or the I/O interfaces and devices 204.

The dynamic system 103 may also include the mass storage device 210 for storing software or information (for example, the generated models or data obtained to which the models are applied). Software shall be construed broadly to mean any type of instructions, whether referred to as software, firmware, middleware, microcode, hardware description language, or otherwise. Instructions may include code (for example, in source code format, binary code format, executable code format, or any other suitable format of code). The instructions, when executed by the one or more processors, cause the processing system to perform the various functions described herein. Accordingly, the dynamic system 103 may include, for example, hardware, firmware, and software, or any combination therein. The mass storage device 210 may include a hard drive, diskette, solid state drive, or optical media storage device. In some embodiments, the mass storage device 210 may be structured such that the data stored therein is easily manipulated and parsed.

As shown in FIG. 6, the dynamic system 103 includes the modeling module 215. As described herein, the modeling module 215 may dynamically generate one or more models for processing data obtained from the data stores or the user. In some embodiments, the modeling module 215 may also apply the generated models to the data. In some embodiments, the one or more models may be stored in the mass storage device 210 or the memory 206. In some embodiments, the modeling module 215 may be stored in the mass storage device 210 or the memory 206 as executable software code that is executed by the processor 202. This, and other modules in the dynamic system 103, may include components, such as hardware and/or software components, object-oriented software components, class components and task components, processes, functions, attributes, procedures, subroutines, segments of program code, drivers, firmware, microcode, circuitry, data, databases, data structures, tables, arrays, and variables. In the embodiment shown in FIG. 6, the dynamic system 103 is configured to execute the modeling module 215 to perform the various methods and/or processes as described herein.

In some embodiments, the report module 216 may be configured to generate a report, notification, or output mentioned and further described herein. In some embodiments, the report module 216 may utilize information received from the dynamic system 103, the data acquired from the data stores, and/or the computing device 102 or the user of the computing device 106 or the computing device 102 of FIG. 5 to generate the report, notification, or output for a specific doctor, nurse, medical administrator, medical researcher, or other medical entity. For example, the dynamic system 103 may receive information that the doctor, nurse, medical administrator, medical researcher, or other medical entity provides via the network 110 that the dynamic system 103 uses to acquire information from the data stores and generate models for processing of the information. In some embodiments, the generated report, notification, or output may include a data file including pertinent medical information related to a recommended treatment regimen to use to treat an input infection for a particular patient. In some embodiments, the report module 216 may include information received from the user in the generated report, notification, or output. In some embodiments, the report module 216 or the processor 202 may generate the notifications 122 referenced in FIG. 2.

The dynamic system 103 also includes the user interface module 214. In some embodiments, the user interface module 214 may also be stored in the mass storage device 210 as executable software code that is executed by the processor 202. In the embodiment shown in FIG. 6, the dynamic system 103 may be configured to execute the user interface module 214 to perform the various methods and/or processes as described herein.

The user interface module 214 may be configured to generate and/or operate user interfaces of various types. In some embodiments, the user interface module 214 constructs pages, applications or displays to be displayed in a web browser or computer/mobile application. In some embodiments, the user interface module 214 may provide an application or similar module for download and operation on the computing device 102 and/or the computing devices 106, through which the user may interface with the dynamic system 103 to obtain the desired report or output. The pages or displays may, in some embodiments, be specific to a type of device, such as a mobile device or a desktop web browser, to maximize usability for the particular device. In some embodiments, the user interface module 214 may also interact with a customer-side application, such as a mobile phone application, a standalone desktop application, or user communication accounts (for example, e-mail or SMS messaging) and provide data as necessary to display medication or infection notifications.

For example, as described herein, the dynamic system 103 may be accessible to the specific doctor, nurse, medical administrator, medical researcher, or other medical entity via a website. In some embodiments, the user may select or opt out of receiving any report or output.

Once the dynamic system 103 receives the user inputs (for example, the identified infection, data timeframe of interest, geographic region, treatment regimen of interest), the user may view the received information via the I/O interfaces and devices 204 and/or the user interface module 214. Once the dynamic system 103 receives the information from the data stores (for example, via the I/O interfaces and devices 204 or via the user interface module 214), the processor 202 or the modeling module 215 may store the received inputs and information in the memory 206 and/or the mass storage device 210. In some embodiments, the received information from the data stores may be parsed and/or manipulated by the processor 202 of the dynamic system 103 (for example, filtered or similarly processed).

In some embodiments, the processor 202 or the modeling module 215 may generate the dynamic model 120 described above in reference to FIG. 2.

The various components of the dynamic system 103 may be coupled together by a bus system 218. The bus system 218 may include a data bus, for example, as well as a power bus, a control signal bus, and a status signal bus in addition to the data bus. In different embodiments, the bus could be implemented in Peripheral Component Interconnect ("PCP"), Microchannel, Small Computer System Interface ("SCSI"), Industrial Standard Architecture ("ISA") and Extended ISA ("EISA") architectures, for example. In addition, the functionality provided for in the components and modules of the dynamic system 103 may be combined into fewer components and modules or further separated into additional components and modules than that shown in FIG. 6.

Example Use Case—Systems and Methods Using Dynamically Updated Infection Data

As described in brief above, the system 100 may be used in a variety of environments to perform database updates and to dynamically generate custom models. As one non-limiting example which is discussed above and herein, the system 100 may be used to process infection and treatment regimen data. Medical entities involved in patient care (for example, doctors, pharmacists, nurses, medical administrators, and medical researchers) are always working to maintain the latest best practices. In some instances, this includes maintaining awareness of drug efficacy against infections and diseases and tracking the infections and diseases within geographic areas of interest. As medications are used to treat various sources of infections, illnesses, and diseases, those sources may develop resistance(s) to the medications. For example, drug resistant bacteria are becoming more common throughout the world as antibiotics are used to treat many bacterial infections. In some embodiments, such medication resistances can be geography-specific. For example, different geographic areas may be exposed to different pathogens, or prescribe different medications to treat infections and other illnesses. Thus, pathogens with varying levels of drug resistance may be present in different geographic regions. The differences in resistance impact an efficacy rate or efficacy of a treatment regimen prescribed to treat an infection. Each medication may have a geography-specific, a facility-specific, and a patient-specific efficacy rate for each infection for which the medication is prescribed. For example, penicillin may have a higher efficacy rate for some illnesses than with other bacterial infections. Thus, medications may have different efficacy rates against different illnesses or diseases (for example, regardless of whether the illness or disease is viral, bacterial, fungal, and so forth). Similarly, different strains of penicillin may have different efficacy rates against the different penicillin-resistant bacterial infections.

In some instances, patients that present at a medical facility for diagnosis and/or treatment may have been exposed to an infection-causing pathogen in a different geographic region than the medical facility treating the patient, or in a different medical facility in the same geographic region as the current medical facility. For example, a patient may have become infected while travelling, but only started to show symptoms or become sick once the patient returns from travel. As another example, the patient may travel from a home area where they were initially infected to a medical facility in a more populated area, to have the illness diagnosed and/or treated. Embodiments of the present disclosure allow the medical entity that is currently treating such a patient (or is interested in disease trends associated with such a patient) to consider infection, medication, and efficacy rate information for different geographic regions than those in which the medical facility exists or is generally exposed. In some embodiments, different patients suffering from the same infections visit different medical facilities for treatment, and thus, no single one medical facility will have all data associated with any infections and/or corresponding treatments for a given geographic region. In some embodiments of the present disclosure, the medical facilities may store the details of the infections associated with patients and treatment regimens used to treat the infections, as well as corresponding results from the treatment and the relative dates for the infection, in patient records. Thus, medical records for patients, for example those stored in the first data store 104, may include details useful for updating efficacy information for medications against particular illnesses in the same and in other medical facilities.

In some embodiments, the doctors, pharmacists, nurses, medical administrators, and medical researchers, associated with the medical facility can perform research on efficacy rates to maintain quality control and develop situation awareness regarding prescription trends. However, such efforts may be time consuming and generally difficult to do manually, as restrictions and system incompatibilities may make accessing patient records from different medical facilities onerous, time-consuming, inefficient, and expensive. Such restrictions and system incompatibilities make it virtually impossible to analyze resistance and antibiotic use trends using real-time data. Furthermore, aggregating sufficient information to accurately update efficacy rates for medications against infections may take substantial amounts of data points, time, and resources (for example, taking up time consuming data processing and computations). Furthermore, the results of such efforts may be unreliable with regard to accurately updating medication efficacy rates and/or even aggregating information from multiple medical facilities. Embodiments of the present disclosure address these shortcomings of prior systems and methods by dynamically responding to customized user inputs with real-time insights and situational awareness gleaned from real-world, large data sets collected over a timeframe that is relevant to the user's request.

In some embodiments, even the patient records regarding details of particular patients, illnesses, and/or medications may be available, but the information is stored in isolated, access-restricted medical records from which pieces of useful information cannot be aggregated or analyzed with other details to generate current information (for example, due to regulations and system incompatibilities). Some patient records may not include information regarding whether the patient fully recovered from the infection based on the prescribed treatment regimen or may not include appropriate details regarding the infection diagnosed or the prescribed treatment regimen. Thus, medical entities that are generally interested in such records may not be able to use the information from the patient records and/or be unable to determine and/or update such efficacy rates. Furthermore, these parties may be unable to identify an optimal treatment regimen to treat an infection based on a particular patient's records, or these parties may not recognize that they have selected a treatment regimen that is not as optimal as an alternate treatment regimen.

Embodiments of the present disclosure address these shortcomings using dynamically-updated data records and user-specified filters to generate insights based on information aggregated over an entire geographic region or facility, where the information has been aggregated over time periods that span the most recent quarters, months, weeks, and days prior to the user's request for information.

Example Use Case—Systems and Methods Using Risk Scores

Embodiments of the system 100 according to the present disclosure generate a risk score for specific patients and generate heat maps (and similar data displays) regarding infections, medication efficacy rates, the geographic spread of the infections, changes in medication efficacy rates, and other valuable, timely insights.

The dynamic system 103 may use a current patient's information or record (hereinafter, current patient record) in combination with the patient records from the first data store 104 and the efficacy rate information from the second data store 108 to generate the risk score. The risk score may indicate a risk that the patient is diagnosed with a particular infection, a risk that the diagnosed infection is caused by a drug-resistant pathogen, a risk that the current patient is resistant to treatment of a particular pathogen using a particular medication, and/or a risk that the diagnosed infection will or will not respond to a particular medication. For example, the current patient's information or record may indicate certain symptoms (and test results when available). The dynamic system 103 of the present disclosure may determine a likelihood that the current patient has a particular infection based on a comparison of the current patient's symptoms and test results with known symptoms and test results for infections, and a comparison with infections that are present in a same geographic region as the current patient. The dynamic system 103 may also determine a risk score representing the likelihood that the current patient's infection is resistant to particular medications or classes of medication. For example, the dynamic system 103 may use the dynamic models to determine the risk score that the current patient is infected with a drug-resistant strain of the infection. A higher risk score may indicate a higher likelihood that the current patient is infected with the drug-resistant strain. In some embodiments, the higher risk score also or alternatively shows a likelihood that a particular treatment regimens will be successful in treating the infection based on the records of similar successful treatment regimens in the same or nearby geographic area of interest.

In some embodiments, the system 100 identifies the risk scores for individual patients, a particular demographic of patients, a particular geographic region, and other groupings of patients. In some embodiments, the system 100 may incorporate prior diagnoses of the patient (or corresponding patient group), details of the medical facility or facilities associated with the diagnoses, and so forth. The system 100 may also determine a risk score representing a likelihood that the current patient is resistant to treatment using a particular drug based on an analysis of the current patient's prior diagnoses, responses to medications, and the current patient's current symptoms and diagnoses.

In some embodiments, the system 100 may use a point scoring system or the determined risk scores to identify a risk of failure of a treatment regimen or medication therapy. For example, if the medication prescribed for treating the identified infection has a high risk score for drug resistance (meaning that the infection is more likely to be resistant to treatment using the prescribed medication), then the system 100 may identify a higher risk of failure. For example, the point scoring system may aggregate risk scores from the infection being resistant to treatment and risk scores that the current patient is resistant to treatment or responds poorly to a particular medication, and a risk that the current patient is infected with a drug-resistant pathogen. Embodiments of the present disclosure can generate and notify medical entities of these risk scores at a critical time in patient care—when the medical entity is first evaluating and weighing treatment regimens based on symptoms the patient is experiencing, in some cases even before a particular infection has been diagnosed.

Embodiments of the present disclosure also provide valuable insights and situational awareness that lead to improved stewardship of diagnostic testing resources. Some infections are difficult, time-consuming, and/or expensive to test. Additionally, drug resistance tests may not cover all relevant, available, or appropriate medications and, thus, some drug-resistant infections may not be addressed by common testing panels. Additionally, varying dosages of medications may not be tested with respect to the drug-resistant infections, even if some level of drug resistance is known or expected for a particular infection. For example, even if a particular strain of MRSA is known to be drug resistant at a particular dosage level of a particular medication, the user may not be aware of other dosages of the medication that are effective against that strain of MRSA or what dosages are ineffective or inappropriate to treat that strain of MRSA. Based on all of the records in the first data store 104 and the second data store 108, the dynamic system 103 and/or the system 100 of the present disclosure may determine and recommend specific medications and/or dosages to prescribe based on the patient information in the first data store 104 and the efficacy information in the second data store 108 without the medical entity having to order a diagnostic test to determine the particular pathogen that is causing a patient's infection. In this way, embodiments of the present disclosure increase stewardship of scarce and often expensive diagnostic testing resources.

Embodiments of the dynamic system 103 and the system 100 of the present disclosure are able to identify when a doctor prescribes an inappropriate or improper treatment regimen to treat an infection of a current patient. The improper treatment regimen can include an inappropriate, suboptimal, or ineffective medication (for example, a medication for which the infection is known to be drug resistant), a dosage that is insufficient to overcome the drug resistance of the infection, and so forth. As such, the dynamic system 103 is able to identify how successful individual doctors are at prescribing appropriate medications for infections they diagnose, how effective a particular medical facility is at prescribing appropriate medications for infections they diagnose and/or treat, and quantities of new/existing medications that are prescribed for treatment. In some embodiments, the dynamic system 103 or the system 100 compares numbers across physicians of a medical facility, physicians of a geographic region, physicians of a particular specialty, or any other suitable grouping, in a dynamic way, as additional patient records are added to or updated in the first data store 104 and/or as the efficacy information in the second data store 108 is added or updated. In some embodiments, the dynamic system 103 or the system 100 generates reports for individual doctors to indicate how often the individual doctor improperly prescribed a medication, and to identify where the doctor can adapt or change routine prescription strategies to improve selection of appropriate treatment regimens at an early stage in patient care (for example, sending the doctor a prompt notifying of an inappropriate selection of treatment regimen, sending the doctor a recommendation of a more optimal treatment regimen, sending a pharmacist or testing clinician a recommendation to intervene early in the doctor's selected treatment regimen by ordering a diagnostic test of a patient sample).

Additional Embodiments

The foregoing description details certain embodiments of the systems, devices, and methods disclosed herein. It will be appreciated, however, that no matter how detailed the foregoing appears in text, the systems, devices, and methods may be practiced in many ways. As is also stated above, it should be noted that the use of particular terminology when describing certain features or aspects of the invention should not be taken to imply that the terminology is being re-defined herein to be restricted to including any specific characteristics of the features or aspects of the technology with which that terminology is associated.

While the above detailed description has shown, described, and pointed out novel features of the development as applied to various embodiments, it will be understood that various omissions, substitutions, and changes in the form and details of the device or process illustrated may be made by those skilled in the art without departing from the spirit of the development. As will be recognized, the present development may be embodied within a form that does not provide all of the features and benefits set forth herein, as some features may be used or practiced separately from others. All changes which come within the meaning and range of equivalency of the claims are to be embraced within their scope.

In general, the word "module," as used herein, refers to logic embodied in hardware or firmware, or to a collection of software instructions, possibly having entry and exit points, written in any programming language described herein. A software module may be compiled and linked into an executable program, installed in a dynamic link library, or may be written in any interpreted programming language. It will be appreciated that software modules may be callable from other modules or from themselves, and/or may be invoked in response to detected events or interrupts. Software modules configured for execution on computing devices may be provided on a computer readable medium, such as a compact disc, digital video disc, flash drive, or any other tangible medium. Such software code may be stored, partially or fully, on a memory device of the executing computing device, such as the dynamic system 103, for execution by the computing device. Software instructions may be embedded in firmware, such as an EPROM. It will be further appreciated that hardware modules may be included of connected logic units, such as gates and flip-flops, and/or may be included of programmable units, such as programmable gate arrays or processors. The modules described herein are preferably implemented as software modules. They may be represented in hardware or firmware. Generally, the modules described herein refer to logical modules that may be combined with other modules or divided into sub-modules despite their physical organization or storage. The modules may be stored on any type of non-transitory computer-readable medium or computer storage device, such as hard drives, solid state memory, optical disc, and/or the like. The systems and modules may also be transmitted as generated data signals (for example, as part of a carrier wave or other analog or digital propagated signal) on a variety of computer-readable transmission mediums, including wireless-based and wired/cable-based mediums, and may take a variety of forms (for example, as part of a single or multiplexed analog signal, or as multiple discrete digital packets or frames). The processes and algorithms may be implemented partially or wholly in application-specific circuitry. The results of the disclosed processes and process steps may be stored, persistently or otherwise, in any type of non-transitory computer storage such as, for example, volatile or non-volatile storage. Skilled artisans may implement the described functionality in varying ways for each particular application, but such implementation decisions should not be interpreted as causing a departure from the scope of the present invention.

A model may generally refer to a machine learning construct which may be used to automatically generate a result or outcome. A model may be trained. Training a model generally refers to an automated machine learning process to generate the model that accepts an input and provides a result or outcome as an output. A model may be represented as a data structure that identifies, for a given value, one or more correlated values. For example, a data structure may include data indicating one or more categories. In such implementations, the model may be indexed to provide efficient look up and retrieval of category values. In other embodiments, a model may be developed based on statistical or mathematical properties and/or definitions implemented in executable code without necessarily employing machine learning.

Machine learning generally refers to automated processes by which received data is analyzed to generate and/or update one or more models. Machine learning may include artificial intelligence such as neural networks, genetic algorithms, clustering, or the like. Machine learning may be performed using a training set of data. The training data may be used to generate the model that best characterizes a feature of interest using the training data. In some implementations, the class of features may be identified before training. In such instances, the model may be trained to provide outputs most closely resembling the target class of features. In some implementations, no prior knowledge may be available for training the data. In such instances, the model may discover new relationships for the provided training data. Such relationships may include similarities between proteins such as protein functions.

A microprocessor may be any conventional general purpose single- or multi-chip microprocessor such as a Pentium® processor, a Pentium® Pro processor, a 8051 processor, a MIPS® processor, a Power PC® processor, or an Alpha® processor. In addition, the microprocessor may be any conventional special purpose microprocessor such as a digital signal processor or a graphics processor. The microprocessor typically has conventional address lines, conventional data lines, and one or more conventional control lines.

The system may be used in connection with various operating systems such as Linux®, UNIX®, MacOS® or Microsoft Windows®.

The system control may be written in any conventional programming language such as C, C++, BASIC, Pascal, .NET (e.g., C#), or Java, and ran under a conventional operating system. C, C++, BASIC, Pascal, Java, and FORTRAN are industry standard programming languages for which many commercial compilers may be used to create executable code. The system control may also be written using interpreted languages such as Perl, Python or Ruby. Other languages may also be used such as PHP, JavaScript, and the like.

With respect to the use of substantially any plural and/or singular terms herein, those having skill in the art may translate from the plural to the singular and/or from the singular to the plural as is appropriate to the context and/or application. The various singular/plural permutations may be expressly set forth herein for sake of clarity.

What is claimed is:

1. A system for selecting a treatment regimen for a particular patient, the system comprising:
   a first data store comprising a first plurality of patient records for a first plurality of patients;

a second data store comprising efficacy rates of a plurality of treatment regimens against a plurality of microbial infections; and a hardware processor configured to execute computer-executable instructions to:

receive, from a user, an indication of a first microbial infection of the particular patient and a first treatment regimen to be prescribed to treat the first microbial infection;

generate a first database comprising a second plurality of patient records by identifying, in the first plurality of patient records of the first data store, patient records associated with diagnosis or treatment of the first microbial infection;

generate a second database comprising the second plurality of patient records appended with efficacy rates for the first microbial infection from the second data store, wherein the efficacy rates indicate a resistance rate of the first microbial infection to the plurality of treatment regimens;

generate a dynamic model configured to determine a likelihood estimation that the first treatment regimen is an appropriate treatment regimen to treat the first microbial infection, wherein the dynamic model is further configured to:

identify, based on the second database, a first efficacy rate of the first treatment regimen to treat the first microbial infection, and identify, from the second database, a second efficacy rate of a second treatment regimen to treat the first microbial infection;

generate a first alert when the identified first efficacy rate is less than a first threshold level or the identified second efficacy rate is greater than a second threshold level; and transmit the first alert to a computing device associated with the user via a wireless communication network, wherein the first alert causes the computing device to activate an application on the computing device to display the first alert to the user, wherein:

the first data store is continuously populated with additional patient records, the efficacy rates of the plurality of treatment regimens against the plurality of microbial infections in the second data store are continuously updated, and the hardware processor is further configured to dynamically and automatically execute computer-executable instructions to:

update the first database and the second database based on patient records of the additional patient records that are associated with the first microbial infection and the efficacy rates for the first microbial infection, and update the first efficacy rate and the second efficacy rate.

2. The system of claim 1, wherein the computer-executable instructions are further configured to receive, from a user, an indication of a healthcare facility, and wherein the second plurality of patient records identified by the computer-executable instructions are patient records associated with the first microbial infection and the indicated healthcare facility.

3. The system of claim 1, wherein the computer-executable instructions are further configured to receive, from a user, an indication of a geographic region, and wherein the second plurality of patient records identified by the computer-executable instructions are patient records associated with the first microbial infection and the indicated geographic region.

4. The system of claim 1, wherein the computer-executable instructions are further configured to receive, from a user, an indication of a time period, and wherein the second plurality of patient records identified by the computer-executable instructions are patient records associated with diagnosis or treatment of the first microbial infection within the indicated time period.

5. The system of claim 1, wherein the computer-executable instructions are configured to filter the second plurality of patient records appended with efficacy rates to comprise patient records associated with at least one of a particular treatment regimen of plurality of treatment regimens, infections related to the first microbial infection, a geographic region, and a healthcare facility.

6. The system of claim 1, wherein the computer-executable instructions are further configured to generate a second alert to the user if, after updating the first efficacy rate and the second efficacy rate, the first efficacy rate falls below the first threshold or the second efficacy rate rises above the second threshold.

7. A computer-implemented method for selecting a treatment regimen for a particular patient using a first data store comprising a first plurality of patient records for a first plurality of patients and a second data store comprising efficacy rates of a plurality of treatment regimens against a plurality of microbial infections, the computer-implemented method comprising:

under control of one or more processors, receiving an indication of a first microbial infection of the particular patient and a first treatment regimen to be prescribed to treat the first microbial infection;

generating a first database comprising a second plurality of patient records by identifying, in the first plurality of patient records of a first data store, patient records associated with diagnosis or treatment of the first microbial infection;

generating a second database comprising the second plurality of patient records appended with efficacy rates for the first microbial infection from the second data store, wherein the efficacy rates for the first microbial infection indicate a resistance rate of the first microbial infection to the plurality of treatment regimens;

generating a dynamic model configured to determine a likelihood estimation that the first treatment regimen is an appropriate treatment regimen to treat the first microbial infection, wherein the dynamic model is further configured to:

identify, based on the second database, a first efficacy rate of the first treatment regimen to treat the first microbial infection, and identify, from the second database, a second efficacy rate of a second treatment regimen to treat the first microbial infection;

generating a first alert when the identified first efficacy rate is less than a first threshold level or the identified second efficacy rate is greater than a second threshold level;

transmitting the first alert to a computing device via a wireless communication network, wherein the first alert causes the computing device to activate an application on the computing device to display the first alert;

updating the first database and the second database based on patient records of the additional patient records that are associated with the first microbial infection, wherein the first data store is continuously populated with additional patient records, and wherein the efficacy rates of the plurality of treatment regimens against the plurality of microbial infections in the second data store are continuously updated; and updating the first efficacy rate and the second efficacy rate.

8. The computer-implemented method of claim 7, further comprising receiving an indication of a healthcare facility, wherein the second plurality of patient records are patient records associated with the first microbial infection and the indicated healthcare facility.

9. The computer-implemented method of claim 8, further comprising receiving an indication of a geographic region, wherein the second plurality of patient records are patient records associated with the first microbial infection and the indicated geographic region.

10. The computer-implemented method of claim 9, further comprising receiving an indication of a time period, wherein the second plurality of patient records are patient records associated with diagnosis or treatment of the first microbial infection within the indicated time period.

11. The computer-implemented method of claim 10, further comprising filtering the second plurality of patient records appended with efficacy rates to comprise patient records associated with at least one of a particular treatment regimen of plurality of treatment regimens, infections related to the first microbial infection, a geographic region, and a healthcare facility.

12. The computer-implemented method of claim 11, further comprising generating a second alert if, after updating the first efficacy rate and the second efficacy rate, the first efficacy rate falls below the first threshold or the second efficacy rate rises above the second threshold.

* * * * *